(12) United States Patent
Gaiba et al.

(10) Patent No.: US 8,314,147 B2
(45) Date of Patent: Nov. 20, 2012

(54) BENZAMIDE DERIVATIVES AS $EP_4$ RECEPTOR AGONISTS

(75) Inventors: Alessandra Gaiba, Harlow (GB); Mark Patrick Healy, Harlow (GB); Christopher Norbert Johnson, Harlow (GB); Susan Roomans, Harlow (GB); Steven James Stanway, Harlow (GB); Martin Edward Swarbrick, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 475 days.

(21) Appl. No.: 12/519,219

(22) PCT Filed: Dec. 12, 2007

(86) PCT No.: PCT/EP2007/063796
§ 371 (c)(1),
(2), (4) Date: Jun. 15, 2009

(87) PCT Pub. No.: WO2008/071736
PCT Pub. Date: Jun. 19, 2008

(65) Prior Publication Data
US 2010/0022650 A1    Jan. 28, 2010

(30) Foreign Application Priority Data

Dec. 15, 2006 (GB) .................................. 0625098.9
Aug. 3, 2007 (GB) .................................. 0715145.9

(51) Int. Cl.
*A61K 31/195* (2006.01)
(52) U.S. Cl. ...................................................... 514/563
(58) Field of Classification Search .................. None
See application file for complete search history.

(56) References Cited

U.S. PATENT DOCUMENTS

2005/0250818 A1  11/2005  Koke et al.
2005/0256170 A1  11/2005  Ocford et al.

FOREIGN PATENT DOCUMENTS

WO    WO 03/000267    *    1/2003
WO    WO 03/015774    *    2/2003

OTHER PUBLICATIONS

STN Search Report (Accession No. 1949:6357) (containing summary of Lockerman et al (Chemische Berichte 80:485-493, 1947 ).*

* cited by examiner

*Primary Examiner* — Craig Ricci
(74) *Attorney, Agent, or Firm* — Robert Steve Thomas

(57) ABSTRACT

A compound of formula (I) or a pharmaceutically acceptable derivative thereof, wherein, $R^1$, $R^2$, $R^3$, $R^4$, $R^5$, m, n and X are as defined in the specification; a process for preparing such compounds; a pharmaceutical composition comprising such compounds; and the use of such compounds in medicine.

2 Claims, No Drawings

BENZAMIDE DERIVATIVES AS EP$_4$ RECEPTOR AGONISTS

CROSS-REFERENCE TO RELATED APPLICATIONS

This application is filed pursuant to 35 USC 371 as a United States National Phase Application of International Patent Application Serial No. PCT/EP2007/063796 filed on Dec. 12, 2007, which claims priority from 625098.9 filed on Dec. 15, 2006 and 0715145.9 filed on Aug. 3, 2007 in the United Kingdom, all of which are incorporated by reference herein in their entireties.

FIELD OF THE INVENTION

This invention relates to benzamide derivatives, to processes for their preparation, to pharmaceutical compositions containing them and to their use in medicine.

The compounds of the present invention are EP$_4$ receptor agonists.

BACKGROUND OF THE INVENTION

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126.

The EP$_4$ receptor is a 7-transmembrane receptor and its natural ligand is the prostaglandin PGE$_2$. PGE$_2$ also has affinity for the other EP receptors (types EP$_1$, EP$_2$ and EP$_3$). The prostanoid EP$_4$ receptor falls into a group of receptors normally associated with elevation of intracellular cyclic adenosine monophosphate (cAMP) levels. The EP$_4$ receptor is associated with smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. Therefore EP$_4$ receptor agonists may be useful for the treatment of pain, inflammation and other conditions associated with the EP$_4$ receptor. The EP$_4$ receptor also plays an important role in closure of the ductus arteriosus, vasodepression, inflammation and bone remodeling as reviewed by Narumiya in *Prostaglandins & Other Lipid Mediators* 2002, 68-69 557-73.

A number of publications have demonstrated that PGE$_2$ acting through the EP$_4$ receptor subtype, and EP$_4$ agonists alone, can regulate inflammatory cytokines after an inflammatory stimulus. Takayama et al in the *Journal of Biological Chemistry* 2002, 277(46), 44147-54 showed PGE$_2$ modulates inflammation during inflammatory diseases by suppressing macrophage derived chemokine production via the EP$_4$ receptor. In *Bioorganic & Medicinal Chemistry* 2002, 10(7), 2103-2110, Maruyama et al demonstrate the selective EP$_4$ receptor agonist (ONO-AE1-437) suppresses LPS induced TNF-α in human whole blood whilst increasing the levels of IL-10. An article from *Anesthesiology*, 2002, 97, 170-176 suggests that a selective EP$_4$ receptor agonist (ONO-AE1-329) effectively inhibited mechanical and thermal hyperalgesia and inflammatory reactions in acute and chronic monoarthritis.

Two independent articles from Sakuma et al in *Journal of Bone and Mineral Research* 2000, 15(2), 218-227 and Miyaura et al in *Journal of Biological Chemistry* 2000, 275 (26), 19819-23, report impaired osteoclast formation in cells cultured from EP$_4$ receptor knock-out mice. Yoshida et al in *Proceedings of the National Academy of Sciences of the United States of America* 2002, 99(7), 4580-4585, by use of mice lacking each of the PGE$_2$ receptor EP subtypes, identified EP$_4$ as the receptor that mediates bone formation in response to PGE$_2$ administration. They also demonstrated a selective EP$_4$ receptor agonist (ONO-4819) consistently induces bone formation in wild type mice. Additionally, Terai et al in *Bone* 2005, 37(4), 555-562 have shown the presence of a selective EP$_4$ receptor agonist (ONO-4819) enhanced the bone-inducing capacity of rhBMP-2, a therapeutic cytokine that can induce bone formation.

Further research by Larsen et al shows the effects of PGE$_2$ on secretion in the second part of the human duodenum is mediated through the EP$_4$ receptor (*Acta. Physiol. Scand.* 2005, 185, 133-140). Also, it has been shown a selective EP$_4$ receptor agonist (ONO-AE1-329) can protect against colitis in rats (Nitta et al in *Scandinavian Journal of Immunology* 2002, 56(1), 66-75). Doré et al in *The European Journal of Neuroscience* 2005, 22(9), 2199-206 have shown that PGE$_2$ can protect neurons against amyloid beta peptide toxicity by acting on EP$_2$ and EP$_4$ receptors. Furthermore Doré has demonstrated in *Brain Research* 2005, 1066(1-2), 71-77 that an EP$_4$ receptor agonist (ONO-AE1-329) protects against neurotoxicity in an acute model of excitotoxicity in the brain.

Woodward et al in *Journal of Lipid Mediators* 1993, 6(1-3), 545-53 found intraocular pressure could be lowered using selective prostanoid agonists. Two papers in Investigative Opthalmology & Visual Science have shown the prostanoid EP$_4$ receptor is expressed in human lens epithelial cells (Mukhopadhyay et al 1999, 40(1), 105-12), and suggest a physiological role for the prostanoid EP$_4$ receptor in modulation of flow in the trabecular framework of the eye (Hoyng et al 1999, 40(11), 2622-6).

Compounds exhibiting EP$_4$ receptor binding activity have been described in, for example, WO98/55468, WO00/18744, WO00/03980, WO00/15608, WO0016760, WO00/21532, EP0855389, EP0985663, WO02/50031, WO02/50032, WO02/50033, WO02/064564, WO03/103604, WO03/077910, WO03/086371, WO04/037813, WO04/067524, WO04/085430, US2004142969, WO05/021508, WO05/105733, WO05/105732, WO05/080367, WO05/037812, WO05/116010, and WO06/122403.

Derivatives of indoprofen such as [4-(1-oxo-1,3-dihydro-2H-benzo[f]isoindol-2-yl)phenyl]-2-propionic acid, sodium salt have been described by Rufer et. al. in *Eur. J. Med. Chem.—Chimica Therapeutica*, 1978, 13, 193.

DETAILED DESCRIPTION

The present invention provides compounds of formula (I) and/or pharmaceutically acceptable derivatives thereof,

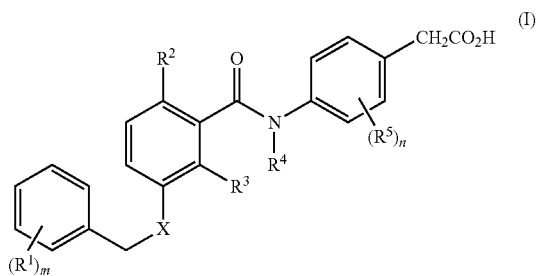

wherein,
$R^1$ represents halogen or $C_{1-4}$ alkyl;
$R^2$ represents $C_{1-4}$ alkyl or chloro;
$R^3$ represents H, $C_{1-4}$ alkyl or halogen;
$R^4$ represents H;
$R^5$ independently each represents halogen or $C_{1-4}$ alkyl;
m represents 0 or 1;
n represents 0, 1 or 2; and
X represents O or NH;
with the proviso that when n represents 2 and $R^5$ represents halogen, the $R^5$ groups together with the phenyl group to which they are attached do not form a 2,3-difluorophenyl moiety.

In one embodiment:
$R^1$ represents halogen;
$R^2$ represents $C_{1-4}$ alkyl or chloro;
$R^3$ represents H, $C_{1-4}$ alkyl or halogen;
$R^4$ represents H;
$R^5$ independently each represents halogen or $C_{1-4}$ alkyl;
m represents 0 or 1;
n represents 0, 1 or 2; and
X represents O or NH;
with the proviso that when n represents 2 and $R^5$ represents halogen, the $R^5$ groups together with the phenyl group to which they are attached do not form a 2,3-difluorophenyl moiety.

In one embodiment of the invention $R^1$ represents halogen, such as chloro. In another embodiment of the invention $R^1$ is attached to the C(2) position of the phenyl ring and represents chloro. In a further embodiment of the invention $R^1$ is attached to the C(3) position of the phenyl ring and represents chloro. In a still further embodiment $R^1$ represents methyl. In a yet further embodiment $R^1$ is methyl and is attached to the C(3) position of the phenyl ring. In another embodiment $R^1$ represents fluoro. In a further embodiment $R^1$ is fluoro and is attached to the C(3) position of the phenyl ring.

In one embodiment $R^2$ represents chloro. In one embodiment of the invention, $R^2$ represents $C_{1-4}$ alkyl. In a further embodiment $R^2$ represents methyl.

In one embodiment of the invention $R^3$ represents H. In another embodiment of the invention $R^3$ represents fluoro.

In one embodiment of the invention $R^5$ represents chloro or fluoro. In another embodiment of the invention $R^5$ represents chloro. In a further embodiment of the invention $R^5$ represents fluoro. In one embodiment of the invention $R^5$ represents $C_{1-4}$ alkyl. In a further embodiment $R^5$ represents methyl. In another embodiment $R^5$ is in the C(3) position on the phenyl ring relative to —$CH_2COOH$. In a still further embodiment $R^5$ represents methyl in the C(3) position on the phenyl ring relative to —$CH_2COOH$.

In one embodiment of the invention m represents 0. In one embodiment of the invention m represents 1.

In one embodiment of the invention n represents 0. In one embodiment of the invention n represents 1. In one embodiment of the invention n represents 2. In another embodiment of the invention n represents 2 and one $R^5$ is fluoro and the other is chloro or fluoro.

In one embodiment of the invention X represents O. In another embodiment of the invention X represents NH.

In one embodiment of the invention:
$R^1$ represents halogen;
$R^2$ is $C_{1-4}$ alkyl;
$R^3$ is H;
$R^5$ represents $C_{1-4}$ alkyl;
m represents 1;
n represents 1; and
X represents O.

In another embodiment of the invention:
$R^1$ represents chloro;
$R^2$ is $C_{1-4}$ alkyl;
$R^3$ is H;
$R^5$ represents $C_{1-4}$ alkyl;
m represents 1;
n represents 1; and
X represents O.

In a further embodiment of the invention:
$R^1$ represents halo;
$R^2$ is methyl;
$R^3$ is H;
$R^5$ represents $C_{1-4}$ alkyl;
m represents 1;
n represents 1; and
X represents O.

In a further embodiment of the invention:
$R^1$ represents chloro;
$R^2$ is methyl;
$R^3$ is H;
$R^5$ represents $C_{1-4}$ alkyl;
m represents 1;
n represents 1; and
X represents O.

In a further embodiment of the invention:
$R^1$ represents chloro;
$R^2$ is methyl;
$R^3$ is H;
$R^5$ represents methyl;
m represents 1;
n represents 1; and
X represents O.

In a further embodiment of the invention:
$R^1$ represents chloro in the C(3) position on the phenyl ring;
$R^2$ is methyl;
$R^3$ is H;
$R^5$ represents methyl in the C(3) position on the phenyl ring relative to —$CH_2COOH$;
m represents 1;
n represents 1; and
X represents O.

In another embodiment of the invention there is provided a compound of formula (I) selected from the group consisting of:
(3-chloro-4-{[(2-chloro-5-{[(3-chlorophenyl)methyl]oxy}phenyl)carbonyl]amino}phenyl)acetic acid;
{3-chloro-4-[({2-chloro-5-[(phenylmethyl)oxy]phenyl}carbonyl)amino]phenyl}acetic acid;
(4-{[(2-chloro-5-{[(3-chlorophenyl)methyl]oxy}phenyl)carbonyl]amino}phenyl)acetic acid;
(4-{[(2-chloro-5-{[(3-chlorophenyl)methyl]oxy}phenyl)carbonyl]amino}-2-fluorophenyl)acetic acid;
(4-{[(2-chloro-5-{[(3-chlorophenyl)methyl]oxy}phenyl)carbonyl]amino}-3-fluorophenyl)acetic acid;
(4-{[(2-chloro-5-{[(3-chlorophenyl)methyl]oxy}phenyl)carbonyl]amino}-2,5-difluorophenyl)acetic acid;
(3-chloro-4-{[(2-chloro-5-{[(3-chlorophenyl)methyl]oxy}phenyl)carbonyl]amino}-2-fluorophenyl)acetic acid;
(4-{[(2-chloro-5-{[(3-chlorophenyl)methyl]oxy}phenyl)carbonyl]amino}-3-methylphenyl)acetic acid;
{4-[({2-chloro-5-[(phenylmethyl)amino]phenyl}carbonyl)amino]phenyl}acetic acid;
(4-{[(2-chloro-5-{[(3-chlorophenyl)methyl]amino}phenyl)carbonyl]amino}phenyl)acetic acid;
(4-{[(2-chloro-5-{[(2-chlorophenyl)methyl]amino}phenyl)carbonyl]amino}phenyl)acetic acid;

(5-chloro-4-{[(2-chloro-5-{[(3-chlorophenyl)methyl]oxy}phenyl)carbonyl]amino}-2-fluorophenyl)acetic acid;
(4-{[(5-{[(3-chlorophenyl)methyl]oxy}-2-methylphenyl)carbonyl]amino}phenyl)acetic acid;
{4-[({2-methyl-5-[(phenylmethyl)oxy]phenyl}carbonyl)amino]phenyl}acetic acid;
(4-{[(6-Chloro-3-{[(3-chlorophenyl)methyl]oxy}-2-fluorophenyl)carbonyl]amino}phenyl)acetic acid;
{4-[({6-chloro-2-fluoro-3-[(phenylmethyl)oxy]phenyl}carbonyl)amino]phenyl}acetic acid;
{3-chloro-4-[({2-methyl-5-[(phenylmethyl)oxy]phenyl}carbonyl)amino]phenyl}acetic acid;
(3-chloro-4-{[(5-{[(3-chlorophenyl)methyl]oxy}-2-methylphenyl)carbonyl]amino}phenyl)acetic acid;
{3-chloro-4-[({6-chloro-2-fluoro-3-[(phenylmethyl)oxy]phenyl}carbonyl)amino]phenyl}acetic acid;
(3-chloro-4-{[(6-chloro-3-{[(3-chlorophenyl)methyl]oxy}-2-fluorophenyl)carbonyl]amino}phenyl)acetic acid;
(4-{[(2-chloro-5-{[(3-fluorophenyl)methyl]oxy}phenyl)carbonyl]amino}-3-methylphenyl)acetic acid;
(4-{[(2-chloro-5-{[(3-fluorophenyl)methyl]oxy}phenyl)carbonyl]amino}-3-fluorophenyl)acetic acid;
(4-{[(5-{[(3-chlorophenyl)methyl]oxy}-2-methylphenyl)carbonyl]amino}-3-fluorophenyl)acetic acid;
(4-{[(5-{[(3-chlorophenyl)methyl]oxy}-2-methylphenyl)carbonyl]amino}-3-methylphenyl)acetic acid;
(4-{[(2-chloro-5-{[(3-methylphenyl)methyl]oxy}phenyl)carbonyl]amino}-3-fluorophenyl)acetic acid;
(4-{[(2-chloro-5-{[(3-methylphenyl)methyl]oxy}phenyl)carbonyl]amino}-3-methylphenyl)acetic acid;
(4-{[(2-chloro-5-{[(2-chlorophenyl)methyl]oxy}phenyl)carbonyl]amino}phenyl)acetic acid;
(3-chloro-4-{[(2-chloro-5-{[(2-chlorophenyl)methyl]oxy}phenyl)carbonyl]amino}phenyl)acetic acid;
(3-chloro-4-{[(2-chloro-5-{[(4-chlorophenyl)methyl]oxy}phenyl)carbonyl]amino}phenyl)acetic acid;
(3-chloro-4-{[(2-chloro-5-{[(3-fluorophenyl)methyl]oxy}phenyl)carbonyl]amino}phenyl)acetic acid;
(3-chloro-4-{[(2-chloro-5-{[(3-methylphenyl)methyl]oxy}phenyl)carbonyl]amino}phenyl)acetic acid;
(3-fluoro-4-{[(5-{[(3-fluorophenyl)methyl]oxy}-2-methylphenyl)carbonyl]amino}phenyl)acetic acid;
(4-{[(5-{[(3-fluorophenyl)methyl]oxy}-2-methylphenyl)carbonyl]amino}-3-methylphenyl)acetic acid;
(3-fluoro-4-{[(2-methyl-5-{[(3-methylphenyl)methyl]oxy}phenyl)carbonyl]amino}phenyl)acetic acid;
(3-chloro-4-{[(2-methyl-5-{[(3-methylphenyl)methyl]oxy}phenyl)carbonyl]amino}phenyl)acetic acid;
(4-{[(2-chloro-5-{[(3-chlorophenyl)methyl]oxy}phenyl)carbonyl]amino}-3,5-difluorophenyl)acetic acid;
(3-methyl-4-{[(2-methyl-5-{[(3-methylphenyl)methyl]oxy}phenyl)carbonyl]amino}phenyl)acetic acid;
(3-chloro-4-{[(5-{[(3-fluorophenyl)methyl]oxy}-2-methylphenyl)carbonyl]amino}phenyl)acetic acid;
(4-{[(6-chloro-3-{[(3-chlorophenyl)methyl]oxy}-2-fluorophenyl)carbonyl]amino}-3-fluorophenyl)acetic acid;
(4-{[(5-{[(3-chlorophenyl)methyl]oxy}-2-methylphenyl)carbonyl]amino}-3,5-difluorophenyl)acetic acid;
(4-{[(6-chloro-3-{[(3-chlorophenyl)methyl]oxy}-2-fluorophenyl)carbonyl]amino}-3-methylphenyl)acetic acid;
(3-chloro-4-{[(6-chloro-2-fluoro-3-{[(3-fluorophenyl)methyl]oxy}phenyl)carbonyl]amino}phenyl)acetic acid;
(4-{[(6-chloro-2-fluoro-3-{[(3-fluorophenyl)methyl]oxy}phenyl)carbonyl]amino}-3-fluorophenyl)acetic acid;
(4-{[(6-chloro-2-fluoro-3-{[(3-fluorophenyl)methyl]oxy}phenyl)carbonyl]amino}-3-methylphenyl)acetic acid;
(4-{[(6-chloro-2-fluoro-3-{[(3-methylphenyl)methyl]oxy}phenyl)carbonyl]amino}-3-fluorophenyl)acetic acid;
and/or a pharmaceutically acceptable derivative thereof.

The present invention covers all combinations of the embodiments described herein.

As used herein, the term 'C$_{1-4}$ alkyl' includes straight chain and branched chain alkyl groups containing 1 to 4 carbon atoms, such as methyl, ethyl, n-propyl, iso-propyl, n-butyl and iso-butyl.

As used herein, 'halogen' means fluorine (or fluoro), chlorine (or chloro), bromine (or bromo) or iodine (or iodo).

By pharmaceutically acceptable derivative is meant any pharmaceutically acceptable salt or ester, or salt of such ester of the compounds of formula (I), or any other compound which upon administration to the recipient is capable of providing (directly or indirectly) a compound of formula (I) or an active metabolite or residue thereof.

It will be appreciated that, for pharmaceutical use, the salts referred to above will be the pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropyl amine, tris(hydroxymethyl)aminomethane, and the like. Salts may also be formed from basic ion exchange resins, for example polyamine resins.

It will be appreciated that the compounds of formula (I) may be produced in vivo by metabolism of a suitable prodrug. Such prodrugs may be for example physiologically acceptable metabolically labile esters of compounds of formula (I). These may be formed by esterification of the carboxylic acid group in the parent compound of formula (I) with, where appropriate, prior protection of any other reactive groups present in the molecule followed by deprotection if required. Examples of such metabolically labile esters include C$_{1-4}$alkyl esters e.g. methyl ethyl or t-butyl esters esters, C$_{3-6}$ alkenyl esters e.g. allyl substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Since the compounds of formula (I) are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates, including solvates of the free acid molecule and solvates of salts derived from the free acid molecule. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The present invention also includes within its scope all isotopically-labelled compounds of formula (I). Such compounds are identical to those recited above except that one or more atoms therein are replaced by an atom having an atomic mass or mass number different from the atomic mass or mass number usually found in nature. Examples of isotopes that can be incorporated into compounds of formula (I) and pharmaceutically acceptable salts thereof include isotopes of hydrogen, carbon, nitrogen, oxygen, chlorine and fluorine, such as $2H$, $3H$, $11C$, $13C$, $14C$, $15N$, $17O$, $18O$, $36Cl$ and $18F$.

Isotopically-labelled compounds of formula (I), for example those into which radioactive isotopes such as $3H$, $14C$ are incorporated, are useful in drug and/or substrate tissue distribution assays. Tritiated, i.e., $3H$, and carbon-14, i.e., $14C$, isotopes are particularly preferred for their ease of preparation and detectability. $11C$ and $18F$ isotopes are particularly useful in PET (positron emission tomography), and are useful in brain imaging. Further substitution with heavier isotopes such as deuterium, i.e., $2H$, can afford certain therapeutic advantages resulting from greater metabolic stability, for example increased in vivo half-life or reduced dosage requirements and, hence, may be preferred in some circumstances. Isotopically labelled compounds of formula (I) may be prepared by carrying out the synthetic procedures disclosed in the Schemes and/or in the Examples below, by substituting a readily available isotopically labelled reagent for a non-isotopically labelled reagent.

The compounds of formula (I) are $EP_4$ receptor agonists and may therefore be useful in treating $EP_4$ receptor mediated diseases. These diseases include those mediated by the action, or loss of action, of $PGE_2$ at $EP_4$ receptors.

In particular the compounds of formula (I) may be useful in the treatment of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula (I) may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD; gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhea, constipation); organ transplantation); other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) may also be useful in the treatment of immunological diseases such as autoimmune diseases, immunological deficiency diseases or organ transplantation. The compounds of formula (I) may also be effective in increasing the latency of HIV infection.

The compounds of formula (I) may also be useful in the treatment of diseases of excessive or unwanted platelet activation such as intermittent claudication, unstable angina, stroke, and acute coronary syndrome (e.g. occlusive vascular diseases).

The compounds of formula (I) may also be useful as a drug with diuretic action, or may be useful to treat overactive bladder syndrome.

The compounds of formula (I) may also be useful in the treatment of impotence or erectile dysfunction.

The compounds of formula (I) may also be useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, calculosis, lithiasis (especially urolithiasis), gout and ankylosing spondylitis, tendinitis and bursitis.

The compounds of formula (I) may also be useful in bone remodeling and/or promoting bone generation and/or promoting fracture healing.

The compounds of formula (I) may also be useful for attenuating the hemodynamic side effects of NSAIDs and COX-2 inhibitors.

The compounds of formula (I) may also be useful in the treatment of cardiovascular diseases such as hypertension or myocardial ischemia; functional or organic venous insufficiency; varicose therapy; hemorrhoids; and shock states associated with a marked drop in arterial pressure (e.g. septic shock).

The compounds of formula (I) may also be useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) may also be useful in the treatment of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of formula (I) may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) may also be useful in the treatment of kidney dysfunction (nephritis, particularly mesangial proliferative glomerulonephritis, nephritic syndrome), liver dysfunction (hepatitis, cirrhosis) and gastrointestinal dysfunction (diarrhea).

It is to be understood that as used herein any reference to treatment includes both treatment of established symptoms and prophylactic treatment.

According to a further embodiment the invention, there is provided a compound of formula (I) or a pharmaceutically acceptable derivative thereof for use in human or veterinary medicine.

According to another embodiment of the invention, there is provided a compound of formula (I) or a pharmaceutically acceptable derivative thereof for use in the treatment of a condition which is mediated by the action, or loss of action, of $PGE_2$ at $EP_4$ receptors.

According to a further embodiment of the invention, there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable derivative thereof.

According to a further embodiment of the invention there is provided a method of treating a human or animal subject suffering from a pain, or an inflammatory, immunological, bone, neurodegenerative or renal disorder, which method comprises administering to said subject an effective amount of a compound of formula (I) or a pharmaceutically acceptable derivative thereof.

According to another embodiment of the invention, there is provided the use of a compound of formula (I) or a pharmaceutically acceptable derivative thereof for the manufacture of a medicament for the treatment of a condition which is mediated by the action, or loss of action, of $PGE_2$ at $EP_4$ receptors.

According to another embodiment of the invention there is provided the use of a compound of formula (I) or a pharmaceutically acceptable derivative thereof for the manufacture of a medicament for the treatment or prevention of a condition such as a pain, or an inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or diluents.

Thus, in another aspect of the invention, there is provided a pharmaceutical composition comprising a compound of formula (I) or a pharmaceutically acceptable derivative thereof adapted for use in human or veterinary medicine.

While it is possible for the compounds of formula (I) or a pharmaceutically acceptable derivative thereof to be administered as the raw chemical, it is preferable to present it as a pharmaceutical formulation. The formulations of the present invention comprise the compounds of formula (I) or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof. Thus, in one embodiment the invention provides a pharmaceutical composition comprising a compound of formula (I) or a pharmaceutically acceptable derivative thereof and a pharmaceutically acceptable carrier or diluent therefor.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy (see for example methods disclosed in 'Remington—The Science and Practice of Pharmacy', 21$^{st}$ Edition, Lippincott, Williams & Wilkins, USA, 2005 and references therein). All methods include the step of bringing into association the compound of formula (I) or a pharmaceutically acceptable acid addition salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for pediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of formula (I) may also be formulated as depot preparations. Such long acting formulations may be administered by implantation (for example subcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The compounds of formula (I) may be used in combination with other therapeutic agents, for example COX-2 inhibitors, such as celecoxib, rofecoxib, valdecoxib or parecoxib; 5-lipoxygenase inhibitors; analgesics such as paracetamol; NSAID's, such as diclofenac, indomethacin, nabumetone, naproxen or ibuprofen; leukotriene receptor antagonists; DMARD's such as methotrexate; sodium channel blockers, such as lamotrigine; N-type calcium channel antagonists; NMDA receptor modulators, such as glycine receptor antagonists; gabapentin, pregabalin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands; $EP_2$ receptor ligands; $EP_3$ receptor ligands; $EP_1$ antagonists; $EP_2$ antagonists and $EP_3$ antagonists; cannabanoid receptor agonists; VR1 antagonists. When the compounds are used in combination with other therapeutic agents, the compounds may be administered either sequentially or simultaneously by any convenient route.

The invention thus provides, in a further embodiment, a combination comprising a compound of formula (I) or a pharmaceutically acceptable derivative thereof together with a further therapeutic agent or agents. In a further embodiment of the invention there is provided a combination comprising an $EP_4$ receptor agonist of formula (I) or a pharmaceutically acceptable derivative thereof and paracetamol.

The combinations referred to above may conveniently be presented for use in the form of a pharmaceutical formulation and thus pharmaceutical formulations comprising a combination as defined above together with a pharmaceutically acceptable carrier or diluent comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

In one embodiment of the invention there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable derivative thereof and paracetamol.

A proposed daily dosage of compounds of formula (I) or their pharmaceutically acceptable salts for the treatment of man is from 0.001 to 30 mg/kg body weight per day and more particularly 0.1 to 3 mg/kg body weight per day, calculated as the free acid, which may be administered as a single or divided dose, for example one to four times per day. The dose range for adult human beings is generally from 0.1 to 1000 mg/day, such as from 10 to 800 mg/day, preferably 10 to 200 mg/day, calculated as the free acid.

A suitable daily dosage of paracetamol is up to 4000 mg per day. Suitable unit doses include 200, 400, 500 and 1000 mg, one, two, three or four times per day.

The precise amount of the compounds of formula (I) administered to a host, particularly a human patient, will be the responsibility of the attendant physician. However, the dose employed will depend on a number of factors including the age and sex of the patient, the precise condition being treated and its severity, the route of administration, and any possible combination therapy that may be being undertaken.

The present invention provides a process for preparing the compounds of formula (I) and pharmaceutically acceptable derivatives thereof.

Thus, in one embodiment there is provided a process for preparing a compound of formula (I) or a pharmaceutically acceptable derivative thereof, which process comprises reacting a compound of formula (II),

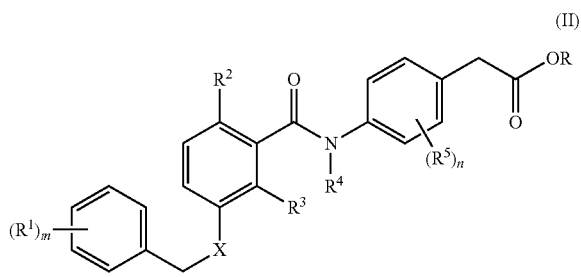

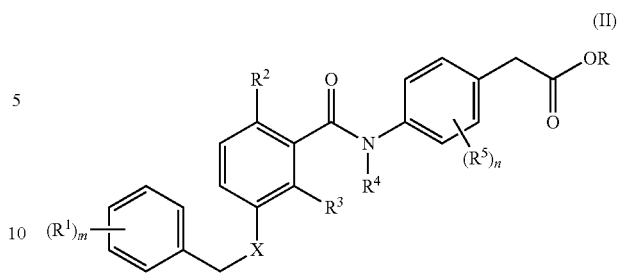

wherein, $R^1$, $R^2$, $R^3$, $R^4$, $R^5$, m, n and X are as defined in formula (I) and R represents a suitable alkyl ester protecting group, such as a methyl, ethyl or benzyl group, with an aqueous acid, and optionally thereafter forming a pharmaceutically acceptable derivative of the compound so formed.

A suitable acid is 2N hydrochloric acid. The above-mentioned reaction involving a compound of formula (II) and an acid may be conveniently carried out in a solvent such as acetic acid, at an elevated temperature, for example 90° C.

In a further embodiment of the invention there is provided a process for preparing a compound of formula (I) or a pharmaceutically acceptable derivative thereof, which process comprises reacting a compound of formula (II), wherein, $R^1$, $R^2$, $R^3$, $R^4$, $R^5$, m, n and X are as defined in formula (I) and R represents a suitable alkyl ester protecting group, such as a methyl, ethyl or benzyl group, with a base and optionally thereafter forming a pharmaceutically acceptable derivative of the compound so formed.

Suitable bases include sodium hydroxide and lithium hydroxide. The above-mentioned reaction involving compound (II) and a base may be conveniently carried out in a solvent or a mixture of solvents, such as methanol/water, ethanol/water or 1,4-dioxane/water. The reaction may be performed at ambient or an elevated temperature.

Compounds of formula (II) where X represents O or NH may be prepared according to Scheme 1 below:

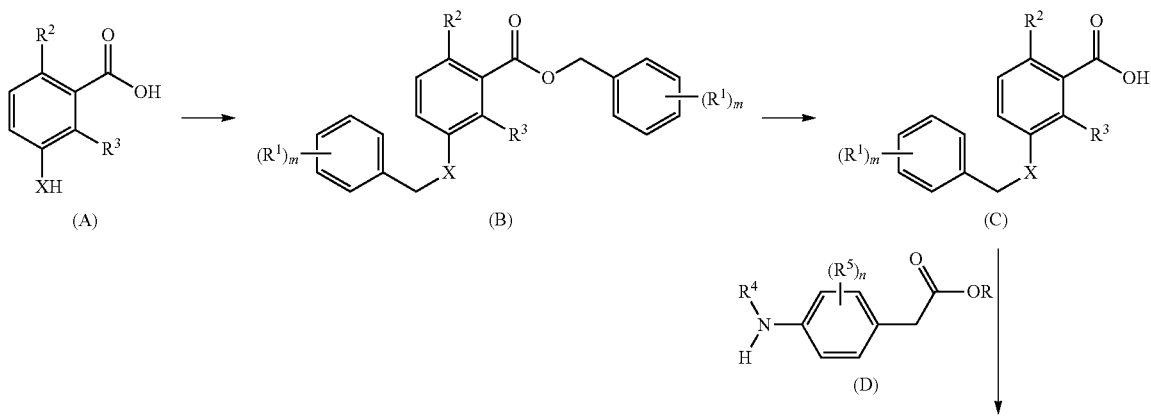

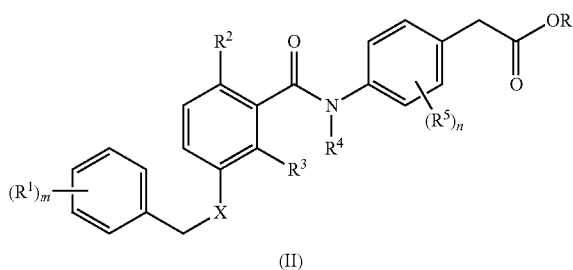

wherein, $R^1$, $R^2$, $R^3$, $R^4$, $R^5$, m, n and X are as defined in formula (I) and R represents a suitable alkyl ester protecting group, such as a methyl, ethyl or benzyl group.

Compounds of formula (II) may be obtained from compounds of formulae (C) and (D) using an amide coupling reagent such as dicyclohexylcarbodiimide or N-(3-dimethylaminopropyl)-N'-ethylcarbodiimide hydrochloride. The Compounds of formula (A) are commercially available or may be prepared in accordance with methods known in the art. For example, 2-chloro-5-hydroxybenzoic acid is available from Apin Chemicals Ltd., UK.

Compounds of formula (II) where X represents NH may also be prepared according to Scheme 2 below:

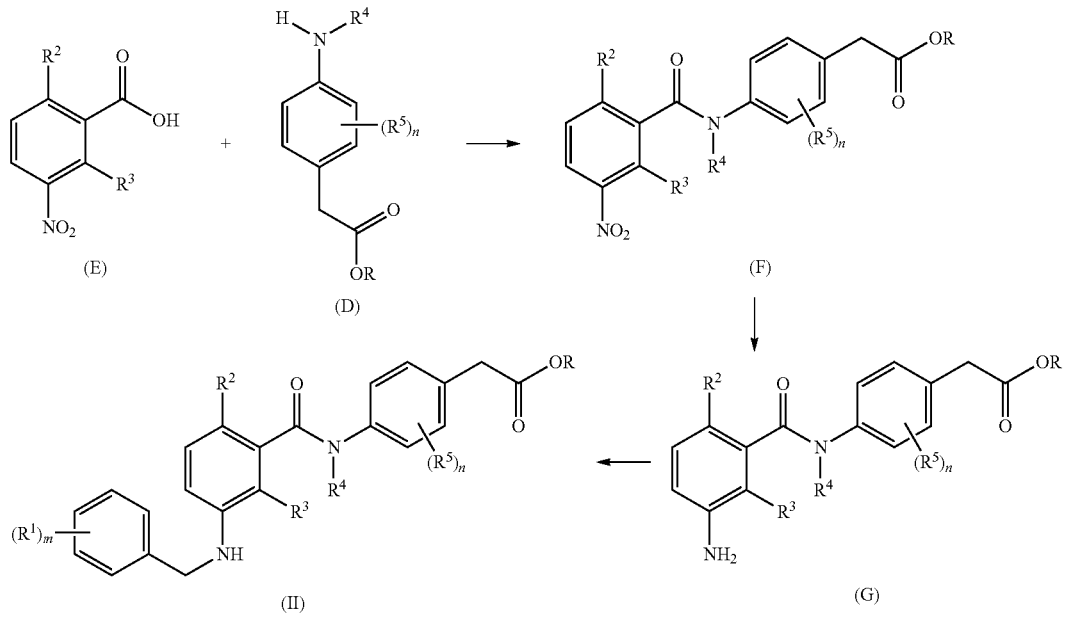

Scheme 2 wherein, $R^1$, $R^2$, $R^3$, $R^4$, $R^5$, m and n are as defined in formula (I) and R represents a suitable alkyl ester protecting group, such as a methyl, ethyl or benzyl group Compounds of formula (II) may be obtained by treating a compound of formula (G) with a benzylating agent, such as a benzyl halide. The reaction is conveniently carried out in a solvent, such as dimethylformamide, in the presence of a base, such as potassium carbonate and at ambient or elevated temperature.

Alternatively, compounds of formula (II) may be obtained by treating a compound of formula (G) with an aldehyde, in the presence of a reducing agent, such as sodium triacetoxyborohydride and in a solvent, such as dichloromethane or dichloroethane. The reaction is typically carried out at low or ambient temperature, and with or without a catalytic quantity of an acid, such as acetic acid.

Compounds of formula (G) may be obtained by reduction of a compound of formula (F) with a mixture of iron powder and acetic acid in a solvent, such as ethanol. The reaction is typically carried out at elevated temperature, for example 80° C.

Compounds of formula (F) may be obtained from compounds of formula (E) by a two-step procedure which entails first converting a compound of formula (E) to an acid chloride. This is conveniently achieved by treating a compound of formula (E) with a reagent such as thionyl chloride or oxalyl chloride at ambient or elevated temperature and with or without a sub-stoichiometric quantity of dimethylformamide. After removal of excess reagent by evaporation and, if necessary, azeotropic distillation with toluene, the crude acid chloride is treated with a compound of formula (D), typically reaction is conveniently carried out in a solvent, such as dichloromethane, with or without a base, such as triethylamine, and at ambient or elevated temperature.

Alternatively, compounds of formula (II) may be obtained from compounds of formula (C) by a two-step procedure which entails first converting a compound of formula (C) to an acid chloride. This is conveniently achieved by treating a compound of formula (C) with a reagent such as thionyl chloride or oxalyl chloride at ambient or elevated temperature, and optionally in the presence of a sub-stoichiometric quantity of dimethylformamide. After removal of excess reagent by evaporation and, if necessary, azeotropic distillation with toluene, the crude acid chloride is treated with a compound of formula (D), typically in a solvent, such as dichloromethane, in the presence of a base, such as pyridine or triethylamine, and at ambient or elevated temperature.

Compounds of formula (D) are commercially available or may be prepared in accordance with methods known in the art. For example, ethyl (4-aminophenyl)acetate is available from Lancaster Synthesis.

Compounds of formula (C) may be conveniently obtained by treating a compound of formula (B) with base, such as lithium hydroxide. The reaction may be conveniently carried out in a mixture of solvents, such as 1,4-dioxane/water, and at ambient or elevated temperature, for example 60° C.

Compounds of formula (B) may be obtained by treating a compound of formula (A) with a benzylating agent, such as a benzyl halide. The reaction is conveniently carried out in a solvent, such as dimethylformamide, in the presence of a base, such as potassium carbonate and at ambient or elevated temperature, for example 60° C.

in a solvent, such as dichloromethane, in the presence of a base, such as pyridine or triethylamine, and at ambient or elevated temperature.

Compounds of formula (E) are commercially available or may be prepared in accordance with methods known in the art. For example, 2-chloro-5-nitrobenzoic acid is available from Apollo Scientific.

Compounds of formula (II) where X represents O may also be prepared according to Scheme 3 below:

Compounds of formula (J) may be obtained from compounds of formula (I) by a two-step procedure which entails first converting a compound of formula (I) to an acid chloride. This is conveniently achieved by treating a compound of formula (I) with a reagent such as thionyl chloride or oxalyl chloride at ambient or elevated temperature and with or without a sub-stoichiometric quantity of dimethylformamide. After removal of excess reagent by evaporation and, if necessary, azeotropic distillation with toluene, the crude acid

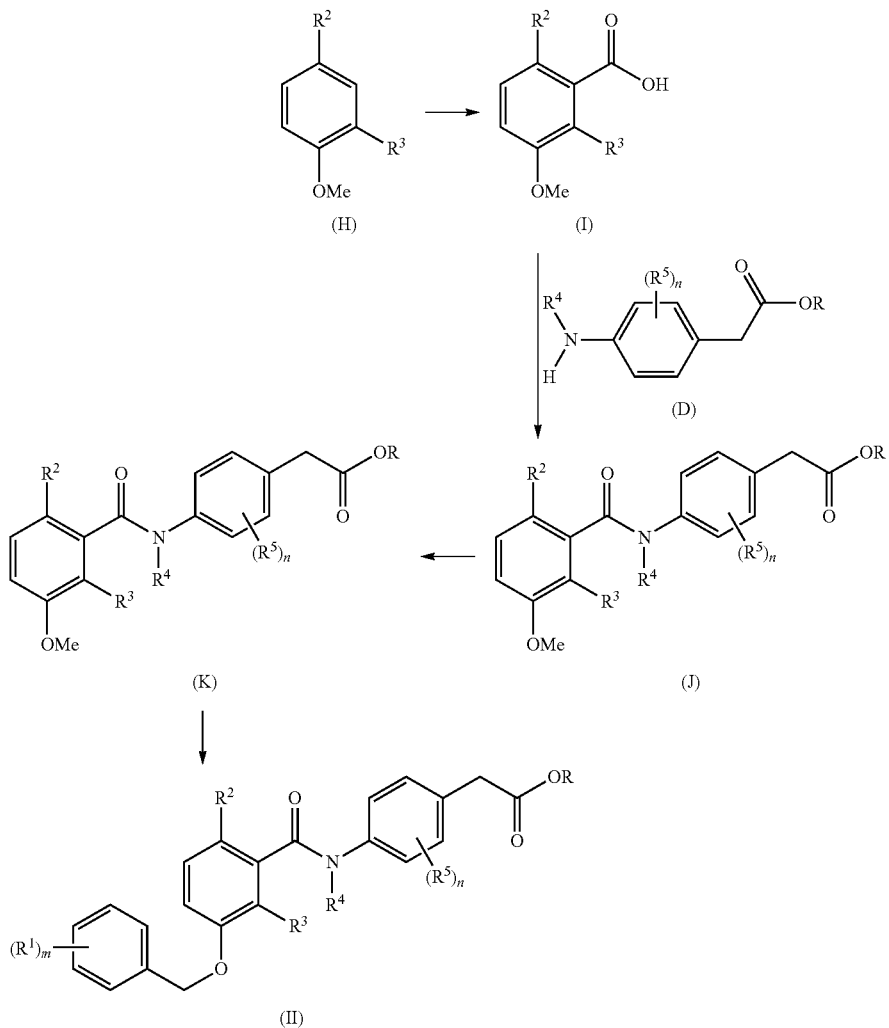

wherein, $R^1$, $R^2$, $R^3$, $R^4$, $R^5$, m and n are as defined in formula (I) and R represents a suitable alkyl ester protecting group, such as a methyl, ethyl or benzyl group Compounds of formula (II) may be obtained by treating a compound of formula (K) with a benzylating agent, such as a benzyl halide. The reaction is conveniently carried out in a solvent, such as dimethylformamide, in the presence of a base, such as potassium carbonate and at ambient or elevated temperature.

Compounds of formula (K) may be obtained by treating a compound of formula (J) with a reagent such as boron tribromide in a solvent, such as dichloromethane and at reduced temperature, for example −78° C. to 0° C.

chloride is treated with a compound of formula (D), typically in a solvent, such as dichloromethane, in the presence of a base, such as pyridine or triethylamine, and at ambient or elevated temperature.

Compounds of formula (I) may be obtained by treating a compound of formula (H) with an organometallic reagent, such as n-butyllithium, followed by solid carbon dioxide. The reaction may be conveniently carried out in a solvent, such as tetrahydrofuran, and at between low temperature (e.g. −78° C.) and ambient temperature.

Compounds of formula (H) are commercially available or may be prepared in accordance with methods known in the art. For example, 4-chloro-2-fluoro-1-(methyloxy)benzene is available from Sigma-Aldrich.

The following examples illustrate the preparation of the compounds of formula (I). The examples show the preparation of intermediates ("Intermediates") and compounds of formula (I) ("Examples"). The starting material for the preparation of intermediates may not necessarily have been prepared from the batch referred to unless expressly indicated. The intermediates for the preparation of the examples may not necessarily have been prepared from the batch referred to unless expressly indicated.

Abbreviations

DCM Dichloromethane
DMAP 4-(Dimethylamino)pyridine
DMF Dimethylformamide
DMSO Dimethylsulfoxide
EtOH Ethanol
EtOAc Ethyl acetate
HCl Hydrochloric acid
LC/MS Liquid chromatography/Mass spectroscopy
MeOH Methanol
MDAP Mass Directed Auto Preparation
NaOH Sodium hydroxide
Analytical Procedures For LC/MS data the 5 minute method is used unless stated otherwise.

LC/MS—5 Minute Method:
Hardware
    Agilent 1100 Gradient Pump
    Agilent 1100 Autosampler
    Agilent 1100 DAD Detector
    Agilent 1100 Degasser
    Agilent 1100 Oven
    Agilent 1100 Controller
    Waters ZQ Mass Spectrometer or Waters ZMD Mass Spectrometer
    Sedere Sedex 75, Sedere Sedex 85 or Polymer Labs PL-ELS-2100
Software
    Waters MassLynx version 4.0 SP2
Column
    The column used is a Waters Atlantis, the dimensions of which are 4.6 mm×50 mm. The stationary phase particle size is 3 μm.
Solvents
A: Aqueous solvent=Water+0.05% Formic Acid
B: Organic solvent=Acetonitrile+0.05% Formic Acid

| Method | |
| --- | --- |
| Time/min | % B |
| 0 | 3 |
| 0.1 | 3 |
| 4 | 97 |
| 4.8 | 97 |
| 4.9 | 3 |
| 5.0 | 3 |

The above method has a flow rate of 3 ml/mins.
The injection volume for the generic method is 5 ul
The column temperature is 30 deg
The UV detection range is from 220 to 330 nm
All retention times are measured in minutes.

LC/MS—2 Minute Method:
Hardware
    Waters Acquity Binary Solvent Manager
    Waters Acquity Sample Manager
    Waters Acquity PDA
    Waters ZQ Mass Spectrometer
    Sedere Sedex 75, Sedere Sedex 85 or Polymer Labs PL-ELS-2100
Software
    Waters MassLynx version 4.1
Column
    Acquity HPLC BEH $C_{18}$ 1.7 μm 2.1 mm×50 mm
    Column oven set to 40 degrees centigrade
Solvents
A: Aqueous solvent=Water 0.1% Formic Acid+10 mM Ammonium Acetate
B: Organic solvent=MeCN:Water 95:5+0.05% Formic Acid
    Weak wash Solvent=MeOH:Water 50:50
    Strong Wash Solvent=MeOH

| Instrument settings | |
| --- | --- |
| Injection volume: | 0.5 μl |
| Injection technique: | Partial loop overfill |
| Weak Wash: | 500 μl |
| Strong Wash: | 500 μl |
| UV detection: | 220 to 330 nm |
| UV sampling rate: | 40 points per second |
| MS scan range: | 100 to 1000 amu |
| MS scanning rate: | 0.2 second scan with a 0.1 second inter scan delay |
| MS scan function: | Electrospray with pos neg switching |
| Cycle time: | 2 minutes and 30 seconds |

| Gradient | | | | |
| --- | --- | --- | --- | --- |
| Time | Flow ml/min | % A | % B | Curve |
| 0 | 1 | 97 | 3 | 6 |
| 0.1 | 1 | 97 | 3 | 6 |
| 1.4 | 1 | 0 | 100 | 6 |
| 1.9 | 1 | 0 | 100 | 6 |
| 2 | 1 | 97 | 3 | 6 |

NMR $^1$H NMR spectra were recorded on a Bruker AVANCE 400 NMR spectrometer or a Bruker DPX250 NMR spectrometer. Chemical shifts are expressed in parts per million (ppm, δ units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Purification Techniques

Purification of the Examples may be carried out by conventional methods such as chromatography and/or recrystallisation using suitable solvents. Chromatographic methods include column chromatography, flash chromatography, HPLC (high performance liquid chromatography), SFC (supercritical fluid chromatography), SCX (strong cation exchange chromatography) and MDAP (mass directed auto-preparation).

The term "Biotage" when used herein refers to commercially available pre-packed silica gel cartridges.

Mass Directed Auto Preparation (MDAP)

Column

Waters Atlantis: 19 mm×100 mm (small scale); and 30 mm×100 mm (large scale).

Stationary phase particle size, 5 μm.

Solvents

A: Aqueous solvent=Water+0.1% Formic Acid

B: Organic solvent=Acetonitrile+0.1% Formic Acid

Make up solvent=Methanol:Water 80:20

Needle rinse solvent=Methanol

Methods

Five methods were used depending on the analytical retention time of the compound of interest:

(1) Large/Small Scale 1.0-1.5=5-30% B
(2) Large/Small Scale 1.5-2.2=15-55% B
(3) Large/Small Scale 2.2-2.9=30-85% B
(4) Large/Small Scale 2.9-3.6=50-99% B Runtime, 13.5 minutes, comprising 10-minute gradient followed by a 3.5 minute column flush and re-equilibration step.

(5) Large/Small Scale 3.6-5.0=80-99% B

Runtime, 13.5 minutes, comprising 6-minute gradient followed by a 7.5 minute column flush and re-equilibration step.

Flow Rate 20 mls/min (Small Scale) or 40 mls/min (Large Scale).

EXAMPLES

Intermediate 1: (3-Chlorophenyl)methyl 2-chloro-5-{[(3-chlorophenyl)methyl]oxy}benzoate

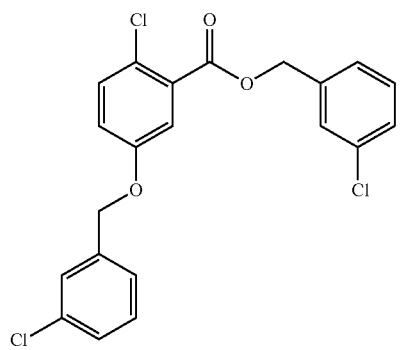

To a mixture of 2-chloro-5-hydroxybenzoic acid (500 mg, 2.9 mmol) in DMF (20 ml) were added potassium carbonate (1.0 g, 7.3 mmol, 2.5 eq) and 3-chlorobenzyl bromide (0.8 ml, 6.1 mmol, 2.1 eq). The mixture was heated at 60° C. for 2.5 hours. On cooling the mixture was diluted with ethyl acetate (300 ml) and washed with water (2×100 ml) then brine (70 ml). Organic layer dried and evaporated in vacuo. The residue was purified by column chromatography (Biotage SP4, 100 g silica column) eluting with 0-30% ethyl acetate in hexanes to afford the title compound as a clear oil (1.16 g). MS (ES+) m/z 421 [M+H]+ $(C_{21}H_{15}{}^{35}Cl_3O_3)$. $^1$H-NMR (400 MHz, $d_6$-DMSO) δ 5.19 (2H, s), 5.35 (2H, s), 7.26 (1H, dd, J 8.8, J 3.2), 7.40-7.56 (10H, m).

Intermediate 2: 2-Chloro-5-{[(3-chlorophenyl)methyl]oxy}benzoic Acid

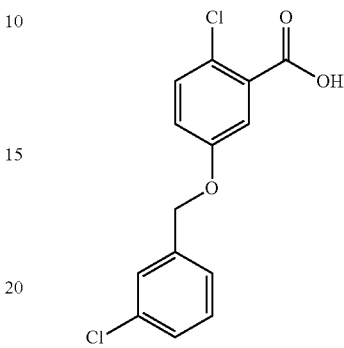

A solution of (3-chlorophenyl)methyl 2-chloro-5-{[(3-chlorophenyl)methyl]oxy}benzoate (970 mg, 2.3 mmol) in dioxane (30 ml) and water (15 ml) was treated with lithium hydroxide (monohydrate) (145 mg, 3.5 mmol, 1.5 eq). The resulting mixture was stirred at room temperature for 2 hours. The solvent was then evaporated in vacuo, the residue take up into water (50 ml) and washed with ether (100 ml). The aqueous layer was then acidified with 2M HCl the extracted with ether (2×150 ml). Organic layers combined, washed with brine, dried and evaporated in vacuo to afford the title product as a white solid (600 mg). MS (ES−) m/z 295 [M−H]− $(C_{14}H_{10}{}^{35}Cl_2O_3)$. $^1$H-NMR (400 MHz, $d_6$-DMSO) δ 5.17 (2H, s), 7.17-7.20 (1H, m), 7.38-7.53 (6H, m), 13.4 (1H, s).

Intermediate 3: Ethyl (4-amino-3-chlorophenyl)acetate

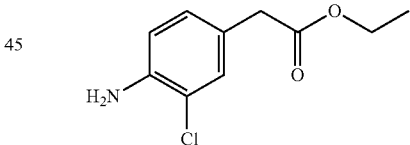

N-chlorosuccinimide (1 eq, 7.45 g, 55.8 mmol) was added to a solution of ethyl 4-aminophenylacetate (10 g, 55.8 mmol) in chloroform (200 mls). The reaction mixture was stirred at room temperature, under argon, for 15 minutes. The reaction mixture was washed with water (250 mls) and the organic layer collected using a hydrophobic frit. This was evaporated to dryness to give a dark brown oil, 9.8 g.

This was purified in 2 batches using the Biotage Horizon, reverse phase 100 g C18 cartridge. The product was eluted using a 5-100% gradient of acetonitrile in water. Approx. 1200 mls solvent was used for each batch.

Clean fractions from the first batch were combined and evaporated to dryness to yield the title compound as a dark red/brown oil, 2.28 g. MS (ES+) m/z 214 [M+H]+ $(C_{10}H_{12}{}^{35}ClNO_2)$. $^1$H-NMR (400 MHz, CDCl$_3$) δ 1.25 (3H, t, J 11.2), 3.47 (2H, s), 4.00 (2H, bs), 4.14 (2H, t, J 12), 6.71 (1H, d, J 13.2), 6.98 (1H, dd, J 13.3, J 3.2), 7.19 (1H, d, J 3.2).

Intermediate 4: Ethyl (3-chloro-4-{[(2-chloro-5-{[(3-chlorophenyl)methyl]oxy}phenyl)carbonyl]amino}phenyl)acetate

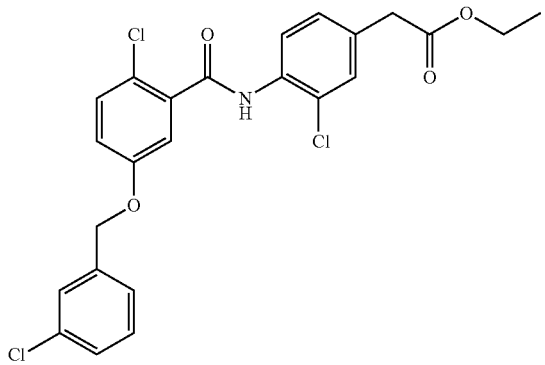

extracted again into dichloromethane (50 ml). Organic layers combined, washed with brine, dried over magnesium sulphate and evaporated to afford the title compound as a yellow oil. The aqueous layer containing an insoluble solid was evaporated in vacuo, the residue purified by SCX cartridge eluting with methanol to afford a further crop of the title compound as a yellow oil (72 mg total). MS (ES+) m/z 492 [M+H]$^+$ (C$_{24}$H$_{20}$$^{35}$Cl$_3$NO$_4$). $^1$H-NMR (400 MHz, d$_6$-DMSO) δ 1.20 (3H, t, J 7.2), 3.72 (2H, s), 4.10 (2H, q, J 7.2), 5.20 (2H, s), 7.15-7.62 (10H, m).

The following intermediates 5 and 6 were prepared in a similar manner to ethyl (3-chloro-4-{[(2-chloro-5-{[(3-chlorophenyl)methyl]oxy}phenyl)carbonyl]amino}phenyl)acetate, without recovering a second crop from the aqueous phase and with additional purification by silica chromatography, as appropriate:

| Int no | Structure | LC | MS | Comments |
|---|---|---|---|---|
| 5 | 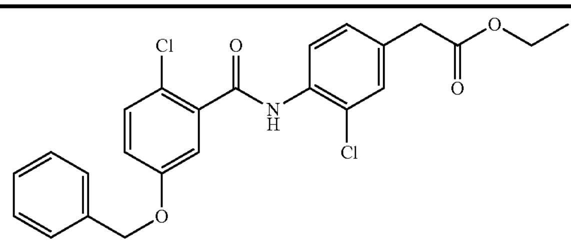 | 3.58 | [C$_{24}$H$_{21}$$^{35}$Cl$_2$NO$_4$ M + H]$^+$ 458 | Same as intermediate 4, no recovery of second crop, additional purification by column chromatography |
| 6 | 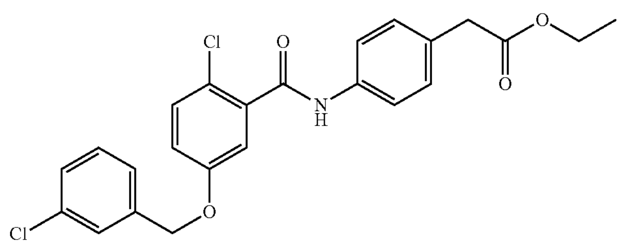 | 3.49 | [C$_{24}$H$_{21}$$^{35}$Cl$_2$NO$_4$ M + H]$^+$ 458 | Same as intermediate 4, no recovery of second crop |

A solution of 2-chloro-5-{[(3-chlorophenyl)methyl]oxy}benzoic acid (230 mg, 0.77 mmol) in dichloromethane (3 ml) was treated with N-[2-(dimethylamino)ethyl]-N'-ethylcarbodiimide hydrochloride (178 mg, 0.93 mmol, 1.2 eq) and stirred at room temperature for 30 minutes. A solution of ethyl (4-amino-3-chlorophenyl)acetate (198 mg, 0.93 mmol, 1.2 eq) in dichloromethane (2 ml) was added and the resulting mixture heated at 40° C. overnight. As some starting material was still present, another 100 mg of N-[2-(dimethylamino)ethyl]-N'-ethylcarbodiimide hydrochloride were added and the mixture heated at 40° C. for another 2 hours. On cooling, the mixture was diluted with dichloromethane (50 ml) and water (30 ml), the layers separated and the aqueous layer

Intermediate 7: Ethyl phenylmethyl (2-fluoro-4-nitrophenyl)propanedioate

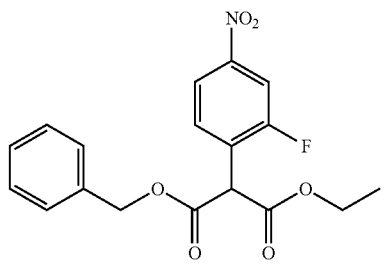

Sodium hydride (504 mg, 12.6 mmol) was added portionwise to an ice bath chilled solution of benzyl ethyl malonate (2.9 g, 12.6 mmol) in dry DMF (20 ml) and stirred for 10 minutes. At room temperature 3,4-difluoronitrobenzene (2 g, 12.6 mmol) was added and stirred under argon. Heated at 100° C. for 20 hours. The reaction mixture was cooled and partitioned between 2N Hydrochloric acid (75 ml) and ethyl acetate (75 ml). The aqueous layer was extracted with ethyl acetate (2×75 ml) and the combined organics were evaporated to a yellow oil. Purified by chromatography on silica gel eluting with ethyl acetate/hexane (1:4) to give the title compound as a yellow oil (3.86 g, 10.6 mmol). LC/MS: Rt=3.40, [MH]+ 362

Intermediate 8: Ethyl (4-amino-2-fluorophenyl)acetate

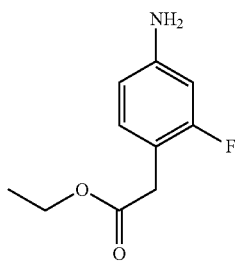

Ethyl phenylmethyl (2-fluoro-4-nitrophenyl)propanedioate (3.86 g, 10.6 mmol) dissolved in ethanol, was treated with ammonium formate (6.7 g, 10.6 mmol) and palladium on carbon 10% paste (380 mg) was added under argon. The reaction mixture was refluxed for 3 hours, cooled and filtered. Evaporated and purified by chromatography on silica gel eluting with ethyl acetate/hexane (1:1) to give the title compound as a yellow oil (1.26 g). LC/MS: Rt=2.10, [MH]+ 198.

The following intermediates 9 and 10 were prepared in a similar manner to ethyl (4-amino-2-fluorophenyl)acetate, using the appropriate starting materials.

| Int No | | LC | MS |
|---|---|---|---|
| 9 | NH₂ structure with F | Rt = 2.20 | [MH]+ 198 |
| 10 | NH₂ structure with CH₃ | 1.46 | For a detailed description for intermediate 10 see below. [MH]+ 194 |

Intermediate 10 was prepared according to the method of intermediate 8 (including the method of intermediate 7) using the appropriate starting materials except for the following differences:

Differences from the Method of Intermediate 7:
Stirred for 30 minutes;
Heated at 100° C. for 5 hours and then overnight;
Extracted with ethyl acetate, washed with water (×2) and brine, dried over sodium sulphate, filtered and then evaporated;
Chromatography was run in a gradient of 10-20% ethyl acetate in hexane.

Differences from the Method of Intermediate 8:
Heated at 60° C. for 2 hours;
Chromatography was run in a gradient of 0 to 50% ethyl acetate in hexane.

Intermediate 11: diethyl (2,5-difluoro-4-nitrophenyl)propanedioate

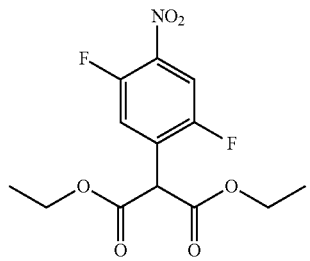

Crushed sodium hydroxide pellets (2.26 g, 56.5 mmol) were added portionwise over 20 minutes to solution of 1,2,4-trifluoro-5-nitrobenzene (5.0 g, 28.2 mmol) and diethyl chloropropanedioate (4.57 ml, 56.5 mmol) in dry DMF (50 ml) at 0° C. under argon. The reaction mixture was allowed to warm to room temperature and stirred overnight. The reaction mixture was cooled to OC and acidified with 2N Hydrochloric acid (50 ml) then extracted with ethyl acetate (150 ml) and washed with water (150 ml). The organic layer was dried over magnesium sulphate, filtered and evaporated to an orange oil. Purified by chromatography on silica gel (Biotage SP4, 100 g silica column) eluting with 0-20% ethyl acetate/hexane to give the title compound as a yellow oil (4.84 g, 15.3 mmol). LC/MS: Rt=3.07, [MH]− 316.

The following intermediates 12 and 13 were prepared in a similar manner to diethyl (2,5-difluoro-4-nitrophenyl)propanedioate using the appropriate starting materials.

| Int No | | LC | MS |
|---|---|---|---|
| 12 | NO₂/Cl/F diethyl propanedioate structure | Rt = 3.21 | [C₁₃H₁₃³⁵ClFNO₆ MH]− 332 |

| Int No | | LC | MS |
|---|---|---|---|
| 13 | NO₂, Cl, F structure with diethyl malonate | Rt = 3.18 | [$C_{13}H_{13}{}^{35}ClFNO_6$ MH]⁻ 332 |

Intermediate 14: diethyl (4-amino-2,5-difluorophenyl)propanedioate

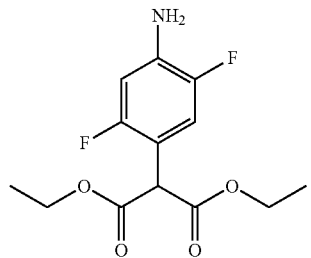

10% Pd/C (wet paste, 484 mg) was added to a solution of diethyl (2,5-difluoro-4-nitrophenyl)propanedioate (4.84 g, 15.3 mmol) and ammonium formate (5 eq, 4.81 g, 76.34 mmol) in ethanol (100 mL). The reaction mixture was heated to reflux under argon for one hour. The reaction was allowed to cool and then filtered through celite to remove the Pd residues. The filtrate was evaporated to dryness and then partitioned between ethyl acetate (100 mL) and water (100 mL). The organic layer was separated, dried over magnesium sulfate, filtered and then evaporated to dryness to give the title compound as an orange oil (4.39 g) LC/MS Rt=1.07 min, [MH]⁺ 288.

The following intermediates 15 and 16 were prepared in a similar manner to diethyl (4-amino-2,5-difluorophenyl)propanedioate using the appropriate starting materials with additional purification by silica chromatography as appropriate:

| Int No | | LC | MS |
|---|---|---|---|
| 15 | NH₂, Cl, F structure with diethyl malonate | Rt = 1.13 | [$C_{13}H_{15}{}^{35}ClFNO_4$ MH]⁺ 304 |

| Int No | | LC | MS |
|---|---|---|---|
| 16 | NH₂, Cl, F structure with diethyl malonate | Rt = 1.13 | [$C_{13}H_{15}{}^{35}ClFNO_4$ MH]⁺ 304 |

Intermediate 17: Ethyl (4-amino-2,5-difluorophenyl)acetate

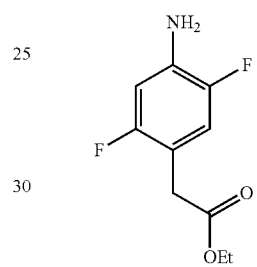

Sodium hydroxide (903 mg, 22.58 mmol) in water (7 ml) was added to a solution of diethyl (4-amino-2,5-difluorophenyl)propanedioate (4.32 g, 15.05 mmol) in ethanol (35 ml). The reaction mixture was heated to 90° C. under argon for 1 hr. The reaction mixture was allowed to cool and then the solvent was evaporated. The residue was acidified (2M HCl, 200 ml) and then extracted with ethyl acetate (200 ml). The organic layer was dried (MgSO₄) and the solvent evaporated. The residue was purified by flash chromatography (Biotage SP4, 40+M, 0→25% ethyl acetate/hexane) to afford the title compound as a pale yellow oil (1.3 g). MS (ES+) m/z 216 [M+H]⁺ ($C_{10}H_{11}FNO_2$).

The following intermediates 18 and 19 were prepared in a similar manner to diethyl (4-amino-2,5-difluorophenyl)propanedioate using the appropriate starting materials:

| Int No | | LC | MS |
|---|---|---|---|
| 18 | NH₂, Cl, F structure with ethyl acetate | Rt = 2.63 | [$C_{10}H_{11}{}^{35}ClFNO_2$ MH]⁺ 232 |

| Int No | | LC | MS |
|---|---|---|---|
| 19 | NH2, Cl, F, ethyl ester structure | Rt = 2.67 | $[C_{10}H_{11}{}^{35}ClFNO_2$ $MH]^+$ 232 |

Intermediate 20: Ethyl (4-{[(2-chloro-5-{[(3-chlorophenyl)methyl]oxy}phenyl)carbonyl]amino}-2-fluorophenyl)acetate

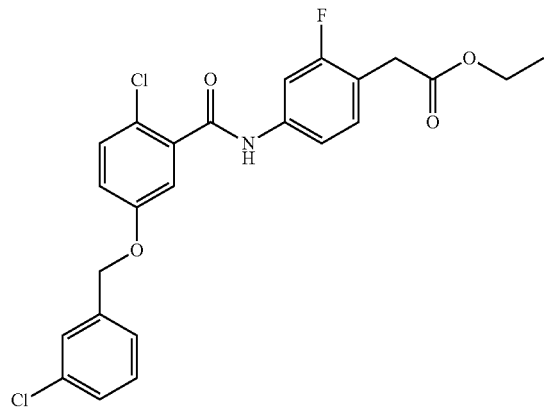

A solution of 2-chloro-5-{[(3-chlorophenyl)methyl]oxy}benzoic acid (207 mg, 0.7 mmol) in dichloromethane (3 ml) was treated with N-[2-(dimethylamino)ethyl]-N'-ethyl-carbodiimide hydrochloride (201 mg, 1.05 mmol, 1.5 eq) and stirred at room temperature for 30 minutes. A solution of ethyl (4-amino-2-fluorophenyl)acetate (207 mg, 1.05 mmol, 1.5 eq) in dichloromethane (2 ml) was added and the resulting mixture heated at 40° C. overnight. On cooling, the mixture was diluted with methanol and purified by SCX cartridge eluting with methanol to afford the title compound as a yellow oil (110 mg). MS (ES+) m/z 476 $[M+H]^+$ ($C_{24}H_{20}{}^{35}Cl_2FNO_4$). $^1$H-NMR (400 MHz, $d_6$-DMSO) δ 1.19 (3H, t, J 7.2), 3.68 (2H, s), 4.09 (2H, q, J 7.2), 5.20 (2H, s), 7.15-7.68 (10H, m).

The following intermediates 21 and 22 and were prepared in a similar manner to ethyl (4-{[(2-chloro-5-{[(3-chlorophenyl)methyl]oxy}phenyl)carbonyl]amino}-2-fluorophenyl)acetate, with the addition of N,N-dimethylaminopyridine (DMAP) as a catalyst, longer heating times as appropriate:

| Int no | Structure | LC | MS | Comments |
|---|---|---|---|---|
| 21 | (structure) | 3.62 | $[C_{24}H_{20}{}^{35}Cl_2FNO_4$ $M + H]^+$ 476 | DMAP added |
| 22 | (structure) | 3.68 | $[C_{24}H_{19}{}^{35}Cl_2F_2NO_4$ $M + H]^+$ 494 | Heated for the weekend,, DMAP added and heated overnight |

Intermediate 23: Ethyl (3-chloro-4-{[(2-chloro-5-{[(3-chlorophenyl)methyl]oxy}phenyl)carbonyl]amino}-2-fluorophenyl)acetate

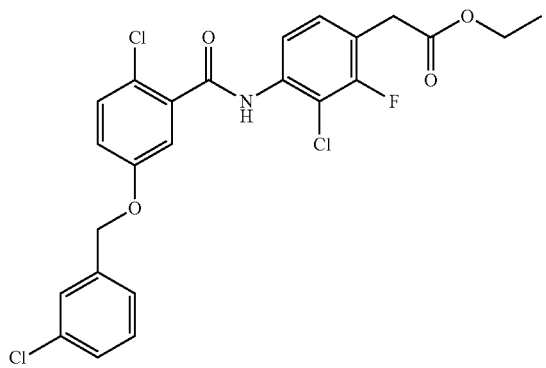

A solution of 2-chloro-5-{[(3-chlorophenyl)methyl]oxy}benzoic acid (200 mg, 0.67 mmol) in dichloromethane (3 ml) was treated with oxalyl chloride (90 ul, 1.0 mmol) and DMF (1 drop). Effervescence was observed and the mixture was stirred at room temperature for 30 minutes. The solvent was then evaporated in vacuo and azeotroped with toluene. The resulting solid was dissolved in dichloromethane (3 ml) and treated with triethylamine (140 ul, 1.0 mmol) and a solution of ethyl (4-amino-3-chloro-2-fluorophenyl)acetate (230 mg, 1.0 mmol) in dichloromethane (2 ml). The mixture was stirred at room temperature for 2 hours. The mixture was then diluted with acetonitrile and purified by SCX cartridge eluting with acetonitrile. Fractions combined and evaporated, residue purified by MDAP to give the title compound as a white solid (110 mg). MS (ES+) m/z 510 [M+H]$^+$ ($C_{24}H_{19}{}^{35}Cl_3FNO_4$). $^1$H-NMR (400 MHz, $d_6$-DMSO) δ 1.20 (3H, t, J 7.2), 3.81 (2H, s), 4.12 (2H, q, J 7.2), 5.20 (2H, s), 7.16-7.55 (9H, m).

The following intermediates 24 to 27 were prepared in a similar manner to ethyl (3-chloro-4-{[(2-chloro-5-{[(3-chlorophenyl)methyl]oxy}phenyl)carbonyl]amino}-2-fluorophenyl)acetate with longer reaction times, aqueous work up, or without the need for purification by MDAP as appropriate:

| Int no | Structure | LC | MS | Comments |
|---|---|---|---|---|
| 24 | 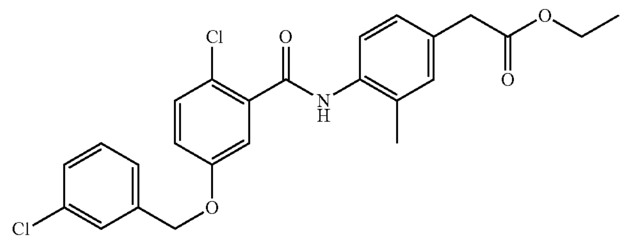 | 3.50 | [$C_{25}H_{23}{}^{35}Cl_2NO_4$ M + H]$^+$ 472 | Same as intermediate 23, no MDAP purification |
| 25 | 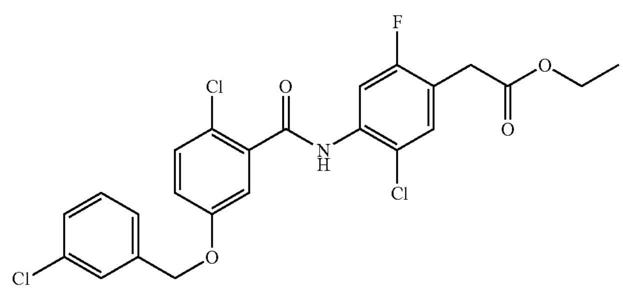 | 3.84 | [$C_{24}H_{19}{}^{35}Cl_3FNO_4$ M + H]$^+$ 510 | Same as intermediate 23, stirred at RT overnight |
| 26 | 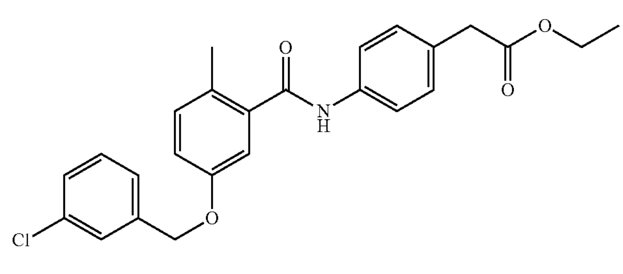 | 1.35 (2 min) | [$C_{25}H_{24}{}^{35}ClNO_4$ M + H]$^+$ 438 | Same as intermediate 23, stirred over weekend, aqueous work up before SCX |

| Int no | Structure | LC | MS | Comments |
|---|---|---|---|---|
| 27 | 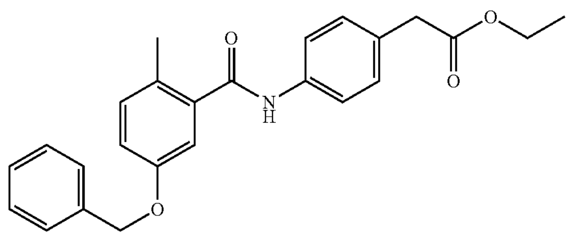 | 1.29 (2 min) | [C$_{25}$H$_{25}$NO$_4$ M + H]$^+$ 404 | Same as intermediate 23, stirred over weekend, aqueous work up before SCX |

Example 1

(3-Chloro-4-{[(2-chloro-5-{[(3-chlorophenyl)methyl]oxy}phenyl)carbonyl]amino}phenyl)acetic Acid

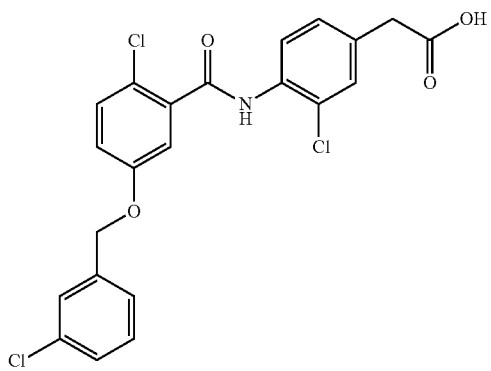

A solution of ethyl (3-chloro-4-{[(2-chloro-5-{[(3-chlorophenyl)methyl]oxy}phenyl)carbonyl]amino}phenyl)acetate (72 mg, 0.15 mmol) in acetic acid (3 ml) and 2M HCl (3 ml) was heated at 90° C. for 2 hours. On cooling water was added and the mixture filtered. The resulting solid was dried in vac oven, then triturated with ether to afford the title compound as an off-white solid (32 mg). MS (ES+) m/z 464 [M+H]$^+$ (C$_{24}$H$_{20}$$^{35}$Cl$_3$NO$_4$). $^1$H-NMR (400 MHz, d$_6$-DMSO) δ 3.63 (2H, s), 5.20 (2H, s), 7.17 (1H, dd, J 8.8, J 2.8), 7.25-7.60 (10H, m), 10.18 (1H, s), 12.5 (1H, s).

The following examples of the invention were prepared in a similar manner to Example 1 from the intermediates described above, with the addition of extra reagent or an organic solvent, longer reaction time and with additional purification by MDAP instead of or in addition to trituration as appropriate:

| Ex no | Structure | LC | MS | Comments |
|---|---|---|---|---|
| 2 | 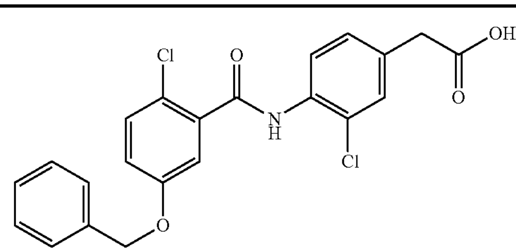 | 3.07 | [C$_{22}$H$_{17}$$^{35}$Cl$_2$NO$_4$ M + H]$^+$ 430 | Purification: solvent evaporated, residue purified by MDAP |
| 3 | 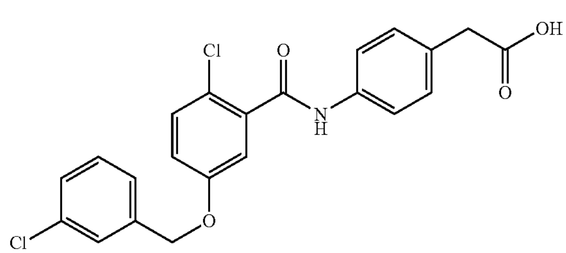 | 3.08 | [C$_{22}$H$_{17}$$^{35}$Cl$_2$NO$_4$ M + H]$^+$ 430 | 2M HCl added (3 ml), heated for 2.5 hours, then additional 2M HCl added (5 ml), then heated for additional 3 hours |

| Ex no | Structure | LC | MS | Comments |
|---|---|---|---|---|
| 4 | 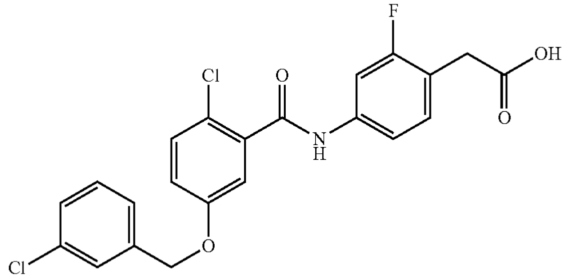 | 3.13 | [C$_{22}$H$_{16}$$^{35}$Cl$_2$FNO$_4$ M + H]$^+$ 448 | no ether trituration |
| 5 | 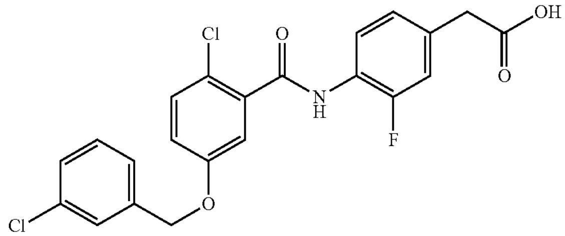 | 3.11 | [C$_{22}$H$_{16}$$^{35}$Cl$_2$FNO$_4$ M + H]$^+$ 448 | trituration with DCM |
| 6 | 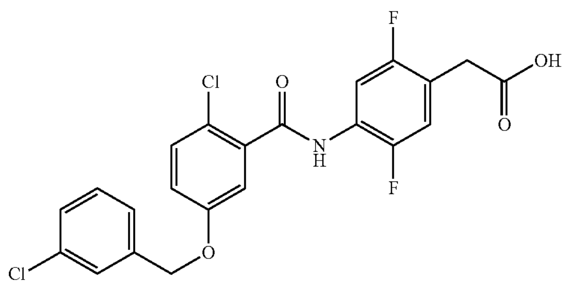 | 3.19 | [C$_{22}$H$_{15}$$^{35}$Cl$_2$F$_2$NO$_4$ M + H]$^+$ 466 | Purification: solvent evaporated, residue purified by MDAP |
| 7 | 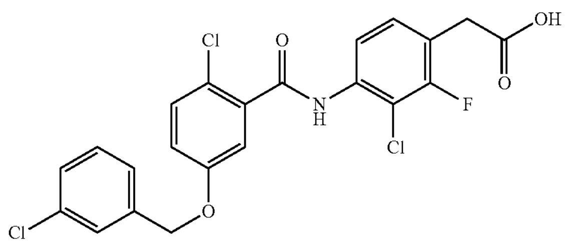 | 1.29 (2 min) | [C$_{22}$H$_{15}$$^{35}$Cl$_3$FNO$_4$ M + H]$^+$ 482 | no ether trituration |
| 8 | 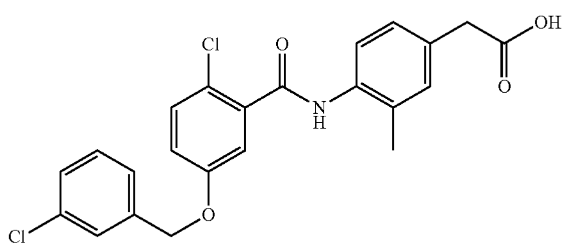 | 1.21 (2 min) | [C$_{23}$H$_{19}$$^{35}$Cl$_2$NO$_4$ M + H]$^+$ 444 | no ether trituration |
| 9 | 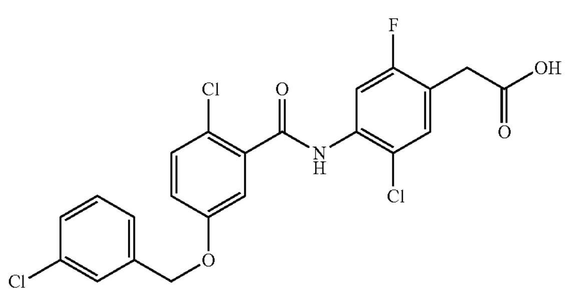 | 3.34 | [C$_{22}$H$_{15}$$^{35}$Cl$_3$FNO$_4$ M + H]$^+$ 482 | Heated for 2 h then dioxane added and heated overnight. Trituration with DCM instead of ether |

| Ex no | Structure | LC | MS | Comments |
|---|---|---|---|---|
| 10 | 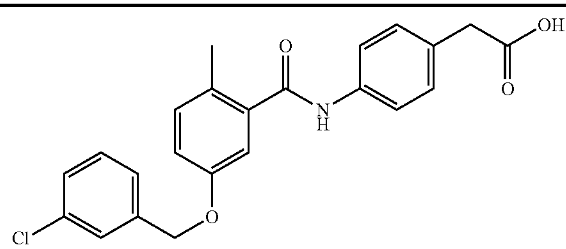 | 1.17 (2 min) | [C₂₃H₂₀³⁵ClNO₄] M + H]⁺ 410 | No ether trituration |
| 11 | 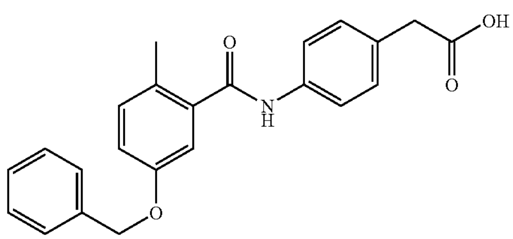 | 1.10 (2 min) | [C₂₃H₂₁NO₄] M + H]⁺ 376 | No ether trituration |

Intermediate 28: Ethyl (4-{[(2-chloro-5-nitrophenyl)carbonyl]amino}phenyl)acetate

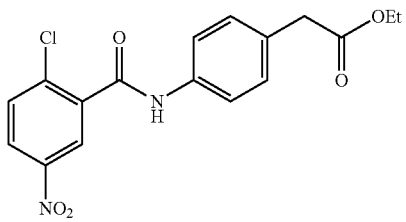

2-Chloro-5-nitrobenzoic acid (1.99 g, 9.87 mmol) was stirred for 18 hrs at 60° C. in thionyl chloride (10 ml). The excess thionyl chloride was removed by evaporation and the crude oil dissolved in chloroform (20 ml). To this solution was added ethyl (4-aminophenyl)acetate (1.18 g, 6.58 mmol) and the reaction was stirred at 60° C. for 18 hrs. The reaction was diluted with water and the phases separated. The organic layer was dried (Na₂SO₄), solvent evaporated and the residue purified by flash chromatography (Biotage SP4, 40+M 0→50% ethylacetate/hexane) to afford the title compound as an off white solid (2.28 g, 96%).

MS (ES+) m/z 363 [M+H]⁺ (C₁₇H₁₅³⁵ClN₂O₅).

$^1$H-NMR (250 MHz, CDCl₃) δ 1.26 (3H, t, J 7), 3.62 (2H, s), 4.14 (2H, q, J 7), 7.30 (2H, d, J 8.5), 7.63 (3H, m), 7.93 (1H, br s), 8.24 (1H, dd, J 9, 3), 8.58 (1H, d, J 3).

Intermediate 29: Ethyl (4-{[(5-amino-2-chlorophenyl)carbonyl]amino}phenyl)acetate

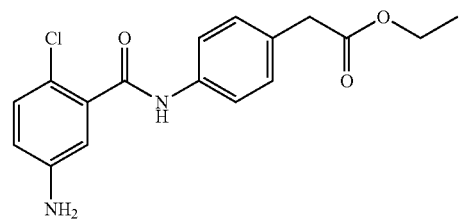

A solution of ethyl (4-{[(2-chloro-5-nitrophenyl)carbonyl]amino}phenyl)acetate (2.27 g, 6.3 mmol) in EtOH (20 ml) was heated at 50° C. A 20% aqueous solution of acetic acid (10 ml) was added followed by iron (6 eq, 37.6 mmol, 2.1 g). The mixture was heated at 80° C. for 30 minutes. On cooling the mixture was filtered through celite washing with EtOH. Solvent evaporated in vacuo. Residue taken up in EtOAc and aqueous sodium bicarbonate. Layers separated, aqueous layer extracted with EtOAc (×2). Organic layers combined and washed with brine, dried over magnesium sulphate and evaporated. The residue was purified by column chromatography (Biotage SP4, 100 g silica column) eluting with 25-75% ethyl acetate in hexanes to afford the title compound as a light yellow oil (1.8 g). MS (ES+) m/z 333 [M+H]⁺ (C₁₇H₁₇³⁵ClN₂O₃). $^1$H-NMR (400 MHz, d₆-DMSO) δ 1.18

(3H, m), 3.61 (2H, s), 4.05 (2H, m), 5.47 (2H, s), 6.65 (2H, m), 7.12 (1H, d, J 8.4), 7.22 (2H, d, J 8.4), 7.64 (2H, m).

Intermediate 30: Ethyl {4-[({2-chloro-5-[(phenylmethyl)amino]phenyl}carbonyl)amino]phenyl}acetate

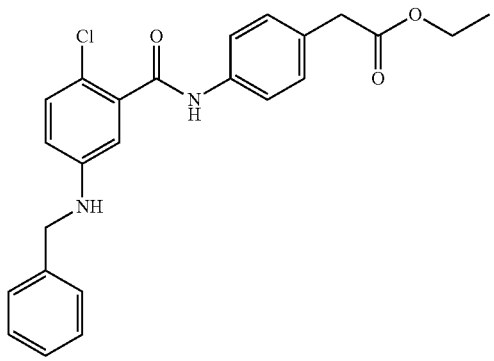

A solution of ethyl (4-{[(5-amino-2-chlorophenyl)carbonyl]amino}phenyl)acetate (300 mg, 0.90 mmol) in DMF (5 ml) was treated with potassium carbonate (152 mg, 1.1 mmol, 1.2 eq) and benzyl bromide (215 ul, 1.8 mmol, 2 eq) and stirred at room temperature overnight. The mixture was diluted with ethyl acetate (150 ml) and washed with water (2×80 ml) and brine (80 ml). Organic layer dried over magnesium sulphate and evaporated in vacuo. The residue was purified by column chromatography (Biotage SP4, 40 g silica column) eluting with 0-25% ethyl acetate in hexanes to afford the title compound as a white solid (90 mg). MS (ES+) m/z 423 [M+H]$^+$ ($C_{24}H_{23}{}^{35}ClN_2O_3$). $^1$H-NMR (400 MHz, $d_6$-DMSO) δ 1.18 (3H, t, J 7.2), 3.61 (2H, s), 4.07 (2H, q, J 7.2), 4.30 (2H, d, J 6), 6.62-7.65 (13H, m).

The following intermediates 31 and 32 were prepared in a similar manner to ethyl {4-[({2-chloro-5-[(phenylmethyl)amino]phenyl}carbonyl)amino]phenyl}acetate, with shorter reaction times where appropriate:

| Int no | Structure | LC | MS | Comments |
|---|---|---|---|---|
| 31 | 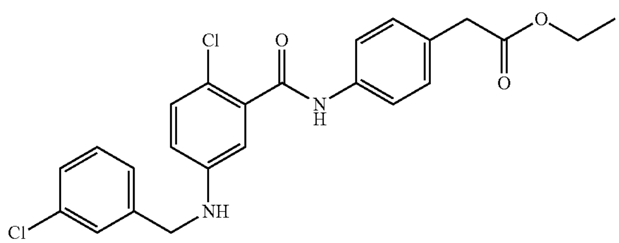 | 3.41 | [$C_{24}H_{22}{}^{35}Cl_2N_2O_3$ M + H]$^+$ 457 | Reaction time 6.5 hours |
| 32 | 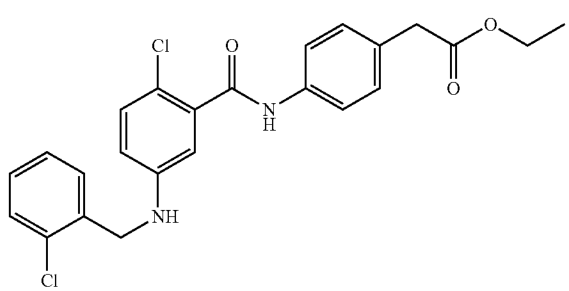 | 3.40 | [$C_{24}H_{22}{}^{35}Cl_2N_2O_3$ M + H]$^+$ 457 | Reaction time 5 hours |

Example 12

{4-[({2-chloro-5-[(phenylmethyl)amino]phenyl}carbonyl)amino]phenyl}acetic Acid

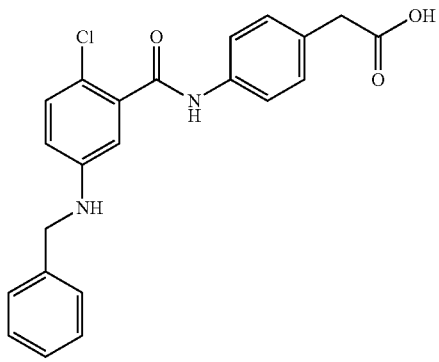

A solution of ethyl {4-[({2-chloro-5-[(phenylmethyl)amino]phenyl}carbonyl)amino]phenyl}acetate (90 mg, 0.21 mmol) in acetic acid (2 ml) and 2M HCl (2 ml) was heated at 90° C. for 2 hours. On cooling water was added then solvent evaporated in vacuo and azeotroped with toluene. The residue was purified by MDAP to afford the title compound as a white solid (40 mg). MS (ES+) m/z 395 [M+H]$^+$ ($C_{22}H_{19}{}^{35}ClN_2O_3$). $^1$H-NMR (400 MHz, $d_6$-DMSO) δ 3.51 (2H, s), 4.30 (2H, d, J 4.4), 6.63-6.73 (3H, m), 7.15-7.36 (10H, m), 10.3 (1H, s).

The following examples of the invention were prepared by a similar method to {4-[({2-chloro-5-[(phenylmethyl)amino]phenyl}carbonyl)amino]phenyl}acetic Acid:

Intermediate 33:
6-Chloro-2-fluoro-3-(methyloxy)benzoic Acid

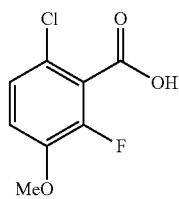

n-Butyllithium (11.7 ml, 18.77 mmol) was added dropwise to a solution of 4-chloro-2-fluoroanisole (2.01 g, 12.52 mmol) in tetrahydrofuran (20 ml) at −78° C. and the reaction was stirred for 30 mins. Crushed solid carbon dioxide was added in one portion and the reaction was then allowed to warm to room temperature. The solvent was evaporated and the residue dissolved in water. Sodium hydroxide (2M to pH~14) was added and the aqueous layer extracted with ethyl acetate. The aqueous layer was acidified with hydrochloric acid (5M, pH~1) and the title compound was collected as a colourless solid (2.25 g, 88%). The compound was dried in vacuo.

MS (ES+) m/z 205 [M+H]$^+$ ($C_8H_6{}^{35}ClFO_3$).

$^1$H-NMR (250 MHz, $d_6$-DMSO) δ 3.87 (3H, s), 7.32 (2H, m), 14.1 (1H, br s).

| Ex no | Structure | LC | MS |
|---|---|---|---|
| 13 | 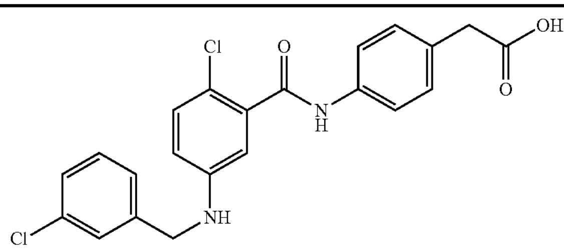 | 2.92 | [$C_{22}H_{18}{}^{35}Cl_2N_2O_3$ M + H]$^+$ 429 |
| 14 | 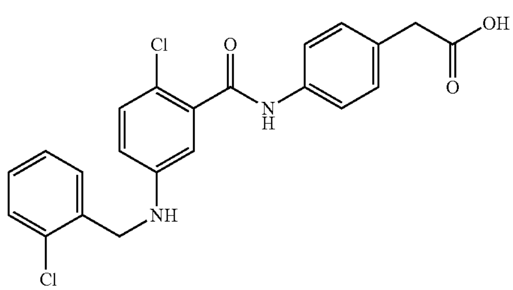 | 2.92 | [$C_{22}H_{18}{}^{35}Cl_2N_2O_3$ M + H]$^+$ 429 |

Intermediate 34: Ethyl[4-({[6-chloro-2-fluoro-3-(methyloxy)phenyl]carbonyl}amino)phenyl]acetate

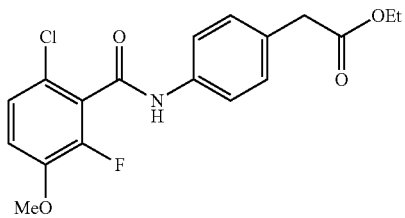

Oxalyl chloride (193 µl, 2.21 mmol) was added dropwise to a solution of 6-chloro-2-fluoro-3-(methyloxy)benzoic acid (300 mg, 1.47 mmol) in dichloromethane (5 ml). To this was added dimethylformamide (1 drop) and the reaction was stirred at room temperature for 3 hrs. The solvent was evaporated to afford a yellow semi-solid. This semi-solid was dissolved in dichloromethane (5 ml) and ethyl (4-aminophenyl) acetate (316 mg, 1.76 mmol) followed by triethylamine (287 µl, 2.06 mmol) were added. The resultant solution was stirred at room temperature overnight. The reaction was diluted with water and the phases separated. The organic layer was dried ($Na_2SO_4$), the solvent evaporated and the residue purified by flash chromatography (Biotage SP4, 25+M silica column, 0→50% ethyl acetate/petrol) to afford the title as a yellow semi-solid (506 mg, 94%). MS (ES+) m/z 366 [M+H$^+$] ($C_{18}H_{17}{}^{35}ClFNO_4$).

$^1$H-NMR (250 MHz, CDCl$_3$) δ 1.26 (3H, t, J 7.25), 3.60 (2H, s), 3.91 (3H, s), 4.13 (2H, q, J 7), 6.97 (1H, t, J 9), 7.17 (1H, dd, J 9, 2), 7.29 (2H, d, J 8.75), 7.45 (1H, br s), 7.59 (2H, m).

Intermediate 35: Ethyl (4-{[(6-chloro-2-fluoro-3-hydroxyphenyl)carbonyl]amino}phenyl)acetate

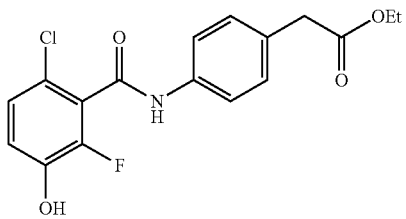

Boron tribromide (393 µl, 4.16 mmol) was added dropwise to a solution of ethyl[4-({[6-chloro-2-fluoro-3-(methyloxy) phenyl]carbonyl}amino)phenyl]acetate (506 mg, 1.39 mmol) in dichloromethane (30 ml) at −78° C. under argon and the reaction was stirred overnight whilst slowly warming to 0° C. The reaction was quenched by the careful addition of water, stirred for 1 hour, further diluted with ethyl acetate, filtered, phases separated, the organic layer dried ($Na_2SO_4$) and solvent evaporated and the residue purified by flash chromatography (Biotage SP4, 25+M silica column, 0→80% ethyl acetate/petrol, clean fractions collected) to afford the title compound as a colourless foam (157 mg, 32%).

MS (ES+) m/z 352 [M+H$^+$] ($C_{17}H_{15}{}^{35}ClFNO_4$).

$^1$H-NMR (250 MHz, CDCl$_3$) δ 1.26 (3H, t, J 7.25), 3.61 (3H, s), 4.14 (2H, q, J 7), 6.99 (1H, t, J 8.75), 7.10 (1H, dd, J 8.75, 1.5), 7.28 (1H, d, J 8.75), 7.57 (2H, m).

Intermediate 36: Ethyl (4-{[(6-chloro-3-{[(3-chlorophenyl)methyl]oxy}-2-fluorophenyl)carbonyl]amino}phenyl)acetate

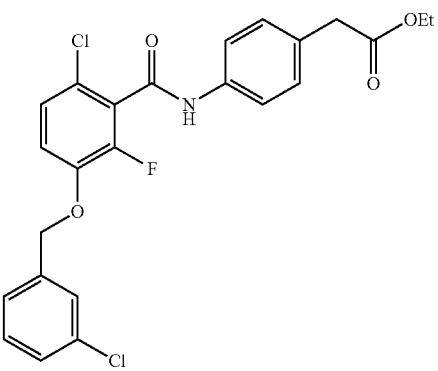

3-Chlorobenzylbromide (28 µl, 0.24 mmol) was added to a suspension of ethyl (4-{[(6-chloro-2-fluoro-3-hydroxyphenyl)carbonyl]amino}phenyl)acetate (80 mg, 0.228 mmol) and potassium carbonate (38 mg, 0.273 mmol) in dimethylformamide (3 ml) and the reaction was stirred at room temperature for 4 hrs. The solvent was evaporated and the residue partitioned between water and ethyl acetate. The organic layer was separated, dried ($Na_2SO_4$) and the solvent evaporated to afford the title compound as a colourless oil (91 mg, 84%).

MS (ES+) m/z 474 [M+H$^+$] ($C_{24}H_{18}{}^{35}Cl_2NO_4$).

$^1$H-NMR (250 MHz, CDCl$_3$) δ 1.25 (3H, t, J 7.25), 3.60 (2H, s), 4.12 (2H, q, J 7.25), 5.11 (2H, s), 6.95 (1H, t, J 8.75), 7.13 (1H, dd, J 8.75, 1.5), 7.33 (6H, m), 7.41 (1H, s), 7.61 (2H, m).

The following intermediate was prepared in a similar manner to Ethyl (4-{[(6-chloro-3-{[(3-chlorophenyl)methyl] oxy}-2-fluorophenyl)carbonyl]amino}phenyl)acetate:

| Int no | Structure | LC | MS |
|---|---|---|---|
| 37 | ![structure] | 1.30 (2 min) | [$C_{24}H_{21}{}^{35}ClFNO_4$] M + H]$^+$ 442 |

Example 15

(4-{[(6-Chloro-3-{[(3-chlorophenyl)methyl]oxy}-2-fluorophenyl)carbonyl]amino}phenyl)acetic Acid

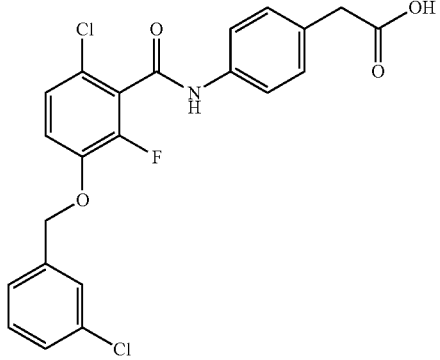

Lithium hydroxide monohydate (12 mg, 0.281 mmol) was added to a solution of ethyl (4-{[(6-chloro-3-{[(3-chlorophenyl)methyl]oxy}-2-fluorophenyl)carbonyl]amino}phenyl)acetate (91 mg, 0.192 mmol in dioxane (2 ml) and water (1 ml) and the reaction was stirred at room temperature overnight. The solvent was evaporated, the residue dissolved in water (5 ml) and acidified (2M HCl, pH~1). The aqueous layer was extracted with ethyl acetate, the organics dried (Na$_2$SO$_4$) and the solvent evaporated to afford a colourless solid which was collected by filtration. This was purified by mass directed auto-prep (MDAP) to afford the title compound as a colourless solid (28 mg, 32%).

MS (ES+) m/z 414 [M+H$^+$] (C$_{22}$H$_{16}$$^{35}$Cl$_2$FNO$_4$).

$^1$H-NMR (250 MHz, d$_6$-DMSO) δ 3.54 (2H, s), 5.26 (2H, s), 7.23 (2H, d, J 5.25), 7.33-7.60 (7H, m), 7.62 (2H, m).

The following example of the invention was prepared in a similar manner to (4-{[(6-Chloro-3-{[(3-chlorophenyl)methyl]oxy}-2-fluorophenyl)carbonyl]amino}phenyl)acetic acid, without the need for MDAP purification:

| Ex no | Structure | LC | MS |
|---|---|---|---|
| 16 | 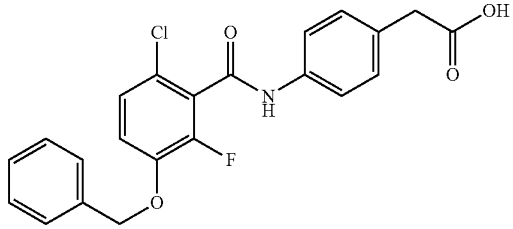 | 1.12 (2 min) | [C$_{22}$H$_{17}$$^{35}$ClFNO$_4$ M + H]$^+$ 414 |

The following intermediate 38 was prepared in a similar manner to (2,5-difluoro-4-nitrophenyl)propanedioate (intermediate 11), using the appropriate starting materials.

| Int No | | LC | MS |
|---|---|---|---|
| 38 | | Rt = 3.06 | [MH]$^+$ 318 |

The following intermediate 39 was prepared in a similar manner to diethyl (4-amino-2,5-difluorophenyl)acetate (intermediate 14), using the appropriate starting materials.

| Int No | | LC | MS |
|---|---|---|---|
| 39 | | Rt = 2.69 | [MH]$^+$ 288 |

The following intermediate 40 was prepared in a similar manner to ethyl (4-amino-2,5-difluorophenyl)acetate (intermediate 17), using the appropriate starting materials.

| Int No | | LC | MS |
|---|---|---|---|
| 40 | [structure: 3,5-difluoroaniline with ethyl acetate group] | Rt = 2.52 | [MH]+ 216 |

Intermediate 41:
6-chloro-2-fluoro-3-hydroxybenzoic Acid

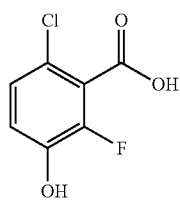

Boron tribromide (1.5 ml, 15.3 mmol) was added dropwise to a solution of 6-chloro-2-fluoro-3-(methyloxy)benzoic acid (intermediate 33, 1.04 g, 5.1 mmol) in dichloromethane (100 ml) at 0° C. under an atmosphere of Argon. The reaction was stirred at room temperature for 18 hrs. Water (5 ml) was added and the solid formed stirred for 5 mins. Sodium hydroxide (2M, 4 ml) was added and the remaining solid dissolved. The layers were separated and the aqueous layer evaporated to afford a colourless solid. This was extracted with ethyl acetate (3×) and the combined organics evaporated to afford the title compound as a yellow solid (831 mg). $^1$H-NMR δ 7.02 (1H, t, J 10), 7.16 (1H, dd, J 10, 3), 10.48 (1H, s), 13.96 (1H, br s).

The following intermediates 42 to 54 were obtained from the appropriate substituted 5-hydroxybenzoic acid by a similar two-step method (alkylation followed by ester hydrolysis) to that used for intermediate 2, with any differences from the described procedures noted in the following table:

| Int No | Structure | LC | MS | Comments |
|---|---|---|---|---|
| 42 | [2-chloro-5-(benzyloxy)benzoic acid] | 2.84 | $[C_{14}H_{11}{}^{35}ClO_3$ $M - H]^-$ 261 | hydrolysis; stirred at room temperature for 3 hours. |
| 43 | [2-methyl-5-((3-chlorobenzyl)oxy)benzoic acid] | 1.20 (2 min) | $[C_{15}H_{13}{}^{35}ClO_3$ $M - H]^-$ 275 | alkylation: 2.0 eq alkylating agent, 2.0 eq $K_2CO_3$; heated 70° C. for 2 hours, then room temp. overnight, then 80° C. for 6 hours. Crude product not purified further. hydrolysis: stirred at room temperature overnight; further LiOH•$H_2O$ (1.5 eq) added; stirred at room temperature overnight. For a detailed description see Intermediates 84 and 85. |
| 44 | [2-methyl-5-(benzyloxy)benzoic acid] | 1.11 (2 min) | $[C_{15}H_{14}O_3$ $M - H]^-$ 241 | alkylation: 2.0 eq alkylating agent, 2.0 eq $K_2CO_3$; heated 70° C. for 2 hours, then room temp. overnight, then 80° C. for 6 hours. Crude product not purified further. hydrolysis: stirred at room temperature overnight; further LiOH•$H_2O$ (1.5 eq) added; stirred at room temperature overnight. |

| Int No | Structure | LC | MS | Comments |
|---|---|---|---|---|
| 45 | 3-chlorobenzyloxy, 2-fluoro, 6-chloro benzoic acid | 1.12 (2 min) | $[C_{14}H_9{}^{35}Cl_2FO_3$ $M - H]^-$ 313 | alkylation: 2.1 eq alkylating agent, 2.4 eq $K_2CO_3$. hydrolysis: heated at 50° C. overnight; acidified with 5 N HCl, precipitated solid collected to furnish product. |
| 46 | benzyloxy, 2-fluoro, 6-chloro benzoic acid | 1.03 (2 min) | $[C_{14}H_{10}{}^{35}ClFO_3$ $M - H]^-$ 279 | alkylation: 2.1 eq alkylating agent, 2.4 eq $K_2CO_3$; crude product not purified further. hydrolysis: heated at 50° C. overnight; acidified with 5 N HCl, precipitated solid collected to furnish product. |
| 47 | 3-fluorobenzyloxy, 2-chloro benzoic acid | 2.85 | $[C_{14}H_{10}{}^{35}ClFO_3$ $M - H]^-$ 279 | alkylation: stirred at room temperature for 67 h. Reaction mixture diluted EtOAc, filtered, washed with water then brine. Crude product not purified further. hydrolysis: stirred 16 hours at room temperature. |
| 48 | 3-methylbenzyloxy, 2-chloro benzoic acid | 2.98 | $[C_{15}H_{13}{}^{35}ClO_3$ $M - H]^-$ 275 | alkylation: stirred at room temperature for 67 h. Reaction mixture diluted EtOAc, filtered, washed with water then brine. Crude product not purified further. hydrolysis: stirred 16 hours at room temperature. |
| 49 | 4-chlorobenzyloxy, 2-chloro benzoic acid | 3.06 | $[C_{14}H_{10}{}^{35}Cl_2O_3$ $M - H]^-$ 295 | alkylation: bromide (2.2 eq). Heated at 80° C. for 3 hous. Further portion of bromide (2.2 eq) added. Heated at 80° C. for a further hour. No brine wash on work-up. Crude product not purified further. hydrolysis: stirred at room temperature for 18 hours. Washed with EtOAc not ether. No brine wash. |
| 50 | 2-chlorobenzyloxy, 2-chloro benzoic acid | 3.02 | $[C_{14}H_{10}{}^{35}Cl_2O_3$ $M - H]^-$ 295 | alkylation: bromide (2.2 eq). Heated at 80° C. for 3 hours. Further portion of bromide (2.2 eq) added. Heated at 80° C. for a further hour. No brine wash on work-up. Crude product not purified further. hydrolysis: stirred at room temperature for 18 hours. Washed with EtOAc not ether. No brine wash. |

| Int No | Structure | LC | MS | Comments |
|---|---|---|---|---|
| 51 | (2-methyl-5-((3-fluorobenzyl)oxy)benzoic acid) | 1.15 (2 min) | [$C_{15}H_{13}FO_3$] $M - H]^-$ 259 | alkylation: stirred at room temperature for 24 hours, further alkylating agent (0.25 eq) added, heated at 65° C. for 24 hours; reaction mixture diluted EtOAc, filtered, washed with water then brine. Crude product not purified further. hydrolysis: stirred at room temperature for 6 hours, heated at 65° C. for 2 hours, then stirred at room temperature for 16 hours. |
| 52 | (2-methyl-5-((3-methylbenzyl)oxy)benzoic acid) | 1.21 (2 min) | [$C_{16}H_{16}O_3$] $M - H]^-$ 255 | alkylation: stirred at room temperature for 24 hours, further alkylating agent (0.25 eq) added, heated at 65° C. for 24 hours; reaction mixture diluted EtOAc, filtered, washed with water then brine. Crude product not purified further. hydrolysis: stirred at room temperature for 6 hours, heated at 65° C. for 2 hours, then stirred at room temperature overnight. |
| 53 | (6-chloro-3-((3-fluorobenzyl)oxy)-2-fluorobenzoic acid) | 2.76 | [$C_{14}H_9{}^{35}ClF_2O_3$] $M - H]^-$ 297 | alkylation: Reaction mixture diluted EtOAc, filtered, washed with sat. aq. $NaHCO_3$ then brine. Crude product not purified further. hydrolysis: stirred at room temperature overnight. |
| 54 | (6-chloro-3-((3-methylbenzyl)oxy)-2-fluorobenzoic acid) | 1.12 (2 min) | [$C_{15}H_{12}{}^{35}ClFO_3$] $M - H]^-$ 293 | alkylation: heated at 65° C. for 2 hours; reaction mixture diluted EtOAc, filtered, washed with water then brine. Crude product not purified further. hydrolysis: heated at 65° C. for 2 hours, then stirred at room temperature overnight; after evaporation, residue taken up in 2 N NaOH then washed/acidified as described. |

The following intermediates 55 to 83 were prepared by a similar two-step method to ethyl (3-chloro-4-{[(2-chloro-5-{[(3-chlorophenyl)methyl]oxy}phenyl)carbonyl]amino}-2-fluorophenyl)acetate (intermediate 23) from the appropriate starting materials with any differences from the described procedure noted in the following table:

| Int No | Compound | LC | MS | Comments |
|---|---|---|---|---|
| 55 | (structure) | 1.37 (2 min) | [C$_{25}$H$_{24}$$^{35}$ClNO$_4$ M + H]+ 438 | Acid chloride formation stirred for 2 hours. Stirred overnight after addition of amine. |
| 56 | (structure) | 1.43 (2 min) | [C$_{25}$H$_{23}$$^{35}$Cl$_2$NO$_4$ M + H]+ 472 | Acid chloride formation stirred for 2 hours. Stirred overnight after addition of amine. |
| 57 | (structure) | 1.34 (2 min) | [C$_{24}$H$_{20}$$^{35}$Cl$_2$FNO$_4$ M + H]$^+$ 476 | Acid chloride formation atirred for 2 hours. Stirred overnight after addition of amine. No azeotrope step. Work up: evaporated to dryness, partitioned between EtOAc and water, organic phase dried and evaporated. Purified by SP4 silica chromatography |
| 58 | (structure) | 1.39 (2 min) | [C$_{24}$H$_{19}$$^{35}$Cl$_3$FNO$_4$ M + H]$^+$ 510 | Acid chloride formation stirred for 2 hours. Stirred overnight after addition of amine. No azeotrope step. Work up: evaporated to dryness, partitioned between EtOAc and water, organic phase dried and evaporated. Purified by SP4 silica chromatography |

| Int No | Compound | LC | MS | Comments |
|---|---|---|---|---|
| 59 | (structure) | 1.34 (2 min) | [M + H]+ 456 (C$_{25}$H$_{23}$ClFNO$_4$) | No MDAP |
| 60 | (structure) | 1.35 (2 min) | [M + H]+ 460 (C$_{24}$H$_{20}$ClF$_2$NO$_4$) | no MDAP |
| 61 | (structure) | 1.39 (2 min) | [C$_{24}$H$_{21}$$^{35}$ClFNO$_4$ M + H]+ 456 | Acid chloride formation stirred for 1 hour. Stirred overnight after addition of amine. No MDAP |
| 62 | (structure) | 1.38 (2 min) | [C$_{25}$H$_{24}$$^{35}$ClNO$_4$ M + H]+ 452 | Acid chloride formation stirred for 1 hour. Stirred overnight after addition of amine. No MDAP For a detailed description see Intermediates 86 and 87 |
| 63 | (structure) | 1.39 (2 min) | [C$_{25}$H$_{23}$$^{35}$ClFNO$_4$ M + H]+ 456 | Acid chloride formation stirred for 1 hour. Stirred overnight after addition of amine. No MDAP |

-continued

| Int No | Compound | LC | MS | Comments |
|---|---|---|---|---|
| 64 | (structure) | 1.37 (2 min) | [C₂₆H₂₆³⁵ClNO₄] M + H]+ 452 | Acid chloride formation stirred for 1 hour. Stirred overnight after addition of amine. No MDAP |
| 65 | (structure) | 1.36 (2 min) | [C₂₄H₂₁³⁵Cl₂NO₄] M + H]+ 458 | Acid chloride formation stirred for 1 hour. Stirred overnight after addition of amine. No MDAP |
| 66 | (structure) | 1.47 (2 min) | [C₂₄H₂₀³⁵Cl₃NO₄] M + H]+ 492 | Acid chloride formation stirred for 1 hour. Stirred overnight after addition of amine. No MDAP |
| 67 | (structure) | 1.47 (2 min) | [C₂₄H₂₀³⁵Cl₃NO₄] M + H]+ 492 | Acid chloride formation stirred for 1 hour. Stirred overnight after addition of amine. No MDAP |

| Int No | Compound | LC | MS | Comments |
|---|---|---|---|---|
| 68 | 2-chloro-5-[(3-fluorobenzyl)oxy]-N-[2-chloro-4-(2-ethoxy-2-oxoethyl)phenyl]benzamide | 1.32 (2 min) | no mass ion detected | Acid chloride formation stirred for 3 hours. Stirred overnight after addition of amine. No azeotrope step. No MDAP |
| 69 | 2-chloro-5-[(3-methylbenzyl)oxy]-N-[2-chloro-4-(2-ethoxy-2-oxoethyl)phenyl]benzamide | 1.38 (2 min) | no mass ion detected | Acid chloride formation stirred for 3 hours. Stirred overnight after addition of amine. No azeotrope step. No MDAP |
| 70 | 5-[(3-fluorobenzyl)oxy]-2-methyl-N-[2-fluoro-4-(2-ethoxy-2-oxoethyl)phenyl]benzamide | 1.33 (2 min) | [M + H]$^+$ 440 (C$_{25}$H$_{23}$F$_2$NO$_4$) | Stirred at room temp o/n after addition amine No MDAP |
| 71 | 5-[(3-fluorobenzyl)oxy]-2-methyl-N-[2-methyl-4-(2-ethoxy-2-oxoethyl)phenyl]benzamide | 1.32 (2 min) | [M + H]$^+$ 436 (C$_{26}$H$_{26}$FNO$_4$) | Stirred at room temp o/n after addition amine No MDAP |

| Int No | Compound | LC | MS | Comments |
|---|---|---|---|---|
| 72 | 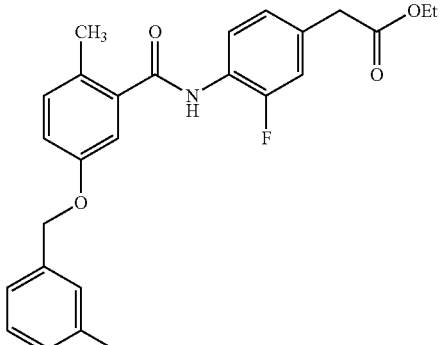 | 1.38 (2 min) | [$C_{26}H_{26}FNO_4$] M + H]+ 436 | Acid chloride formation stirred for 1 hour. Stirred overnight after addition of amine. |
| 73 | 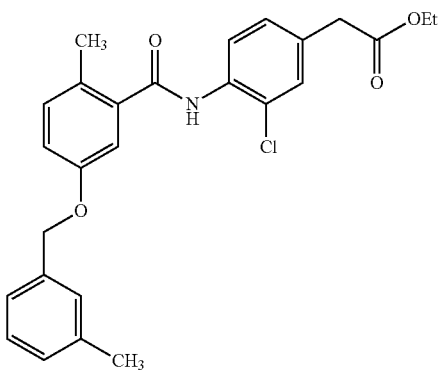 | 1.44 (2 min) | [$C_{26}H_{26}{}^{35}ClNO_4$] M + H]+ 452 | Oxalyl chloride (2 eqs). Stirred room temp 2 hours. No azeotrope step. Aniline (1.1 eqs). Triethylamine (1.3 eqs). Stirred room temp overnight. |
| 74 | 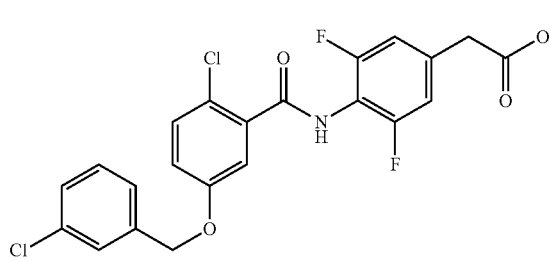 | 1.35 (2 min) | [M + H]$^+$ 494 ($C_{24}H_{19}{}^{35}Cl_2F_2NO_4$) | Stirred at room temp o/n after addition amine Purification by trituration with DCM after SCX (no MDAP) |
| 75 | 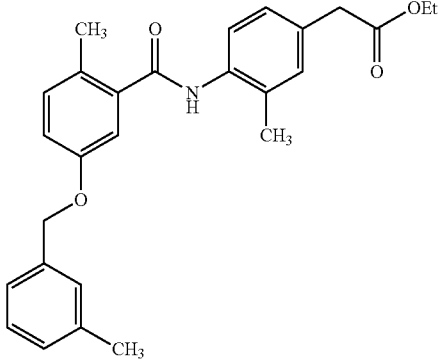 | 1.36 (2 min) | [$C_{27}H_{92}NO_4$] M + H]+ 432 | Acid chloride formation stirred for 1 hour. Stirred overnight after addition of amine. No MDAP |

-continued

| Int No | Compound | LC | MS | Comments |
|---|---|---|---|---|
| 76 | | 1.39 (2 min) | [C$_{25}$H$_{23}$$^{35}$ClFNO$_4$] M + H]+ 456 | Oxalyl chloride (2 eqs). Stirred room temp 2 hours. No azeotrope step. Aniline (1.1 eqs). Triethylamine (1.3 eqs). Stirred room temp overnight. No MDAP |
| 77 | | 1.35 (2 min) | [M + H]$^+$ 494 (C$_{24}$H$_{19}$$^{35}$Cl$_2$F$_2$NO$_4$) | Stirred at room temp o/n after addition amine No MDAP |
| 78 | | 1.36 (2 min) | [C$_{25}$H$_{22}$$^{35}$ClF$_2$NO$_4$ M + H]+ 474 | Acid chloride formation stirred for 2 hours. Pyridine used as base, stirred overnight after addition of amine. No MDAP |
| 79 | | 1.35 (2 min) | [M + H]$^+$ 494 (C$_{25}$H$_{22}$$^{35}$Cl$_2$FNO$_4$) | Stirred at room temp o/n after addition amine No MDAP |
| 80 | | 3.47 (5 min) | [M + H]$^+$ 494 (C$_{24}$H$_{19}$$^{35}$Cl$_2$F$_2$NO$_4$) | Stirred at room temp o/n after addition amine. Eluent for SCX MeOH No MDAP |

-continued

| Int No | Compound | LC | MS | Comments |
|---|---|---|---|---|
| 81 | (structure: 6-chloro-3-[(3-fluorobenzyl)oxy]-2-fluoro-N-[3-fluoro-4-(ethoxycarbonylmethyl)phenyl]benzamide) | 3.38 (5 min) | [M + H]⁺ 478 (C₂₄H₁₉³⁵ClF₃NO₄) | Stirred at room temp o/n after addition amine No MDAP |
| 82 | (structure: 6-chloro-3-[(3-fluorobenzyl)oxy]-2-fluoro-N-[3-methyl-4-(ethoxycarbonylmethyl)phenyl]benzamide) | 3.36 (5 min) | [M + H]⁺ 474 (C₂₅H₂₂³⁵ClF₂NO₄) | Stirred at room temp o/n after addition amine No MDAP |
| 83 | (structure: 6-chloro-3-[(3-methylbenzyl)oxy]-2-fluoro-N-[3-fluoro-4-(ethoxycarbonylmethyl)phenyl]benzamide) | 1.35 (2 min) | [C₂₅H₂₂³⁵ClF₂NO₄] M + H]+ 474 | Acid chloride formation stirred for 1 hour. Stirred over weekend after addition of amine. |

The following examples 17, 18, 21-29 and 40 were prepared in a similar manner to (3-Chloro-4-{[(2-chloro-5-{[(3-chlorophenyl)methyl]oxy}phenyl)carbonyl]amino}phenyl) acetic acid (example 1) from the appropriate starting materials with any differences from the described procedure noted in the following table:

| Ex. No. | Compound | LC (method) | MS | Synthetic route/comments |
|---|---|---|---|---|
| 17 | (structure) | 1.17 (2 min) | [C₂₃H₂₀³⁵ClNO₄] M + H]⁺ 410 | Product precipitated on cooling, collected by filtration and dried under vacuum. |
| 18 | (structure) | 1.24 (2 min) | [C₂₃H₁₉³⁵Cl₂NO₄] M + H]⁺ 444 | Heated at 90° C. for further 2 hours. Product precipitated on cooling, collected by filtration and dried under vacuum. |

-continued

| Ex. No. | Compound | LC (method) | MS | Synthetic route/comments |
|---|---|---|---|---|
| 21 | (2-chloro-5-(3-fluorobenzyloxy)benzamide linked to 3-methylphenylacetic acid) | 2.89 (5 min) | $[C_{23}H_{19}{}^{35}ClFNO_4]$ $M+H]^+$ 428 | same as example 1 |
| 22 | (2-chloro-5-(3-fluorobenzyloxy)benzamide linked to 3-fluorophenylacetic acid) | 1.16 (2 min) | $[C_{22}H_{16}{}^{35}ClF_2NO_4]$ $M+H]^+$ 432 | same as example 1 |
| 23 | (2-methyl-5-(3-chlorobenzyloxy)benzamide linked to 3-fluorophenylacetic acid) | 1.22 (2 min) | $[C_{23}H_{19}{}^{35}ClFNO_4]$ $M+H]^+$ 428 | Allowed to cool to room temperature overnight. No water was added. Product extracted into EtOAc, dried, evaporated and purified by MDAP. |
| 24 | (2-methyl-5-(3-chlorobenzyloxy)benzamide linked to 3-methylphenylacetic acid) | 1.21 (2 min) | $[C_{24}H_{22}{}^{35}ClNO_4]$ $M+H]^+$ 424 | Allowed to cool to room temperature overnight. Product extracted into EtOAc, dried, evaporated and purified by MDAP. For a detailed description see intermediates 84 to 87 and Example 46. |
| 25 | (2-chloro-5-(3-methylbenzyloxy)benzamide linked to 3-fluorophenylacetic acid) | 1.24 (2 min) | $[C_{23}H_{19}{}^{35}ClFNO_4]$ $M+H]^+$ 428 | Allowed to cool to room temperature overnight. Reaction mixture evaporated and purified by MDAP. |
| 26 | (2-chloro-5-(3-methylbenzyloxy)benzamide linked to 3-methylphenylacetic acid) | 1.23 (2 min) | $[C_{24}H_{22}{}^{35}ClNO_4]$ $M+H]^+$ 424 | Allowed to cool to room temperature overnight. Reaction mixture evaporated and purified by MDAP. |

-continued

| Ex. No. | Compound | LC (method) | MS | Synthetic route/comments |
|---|---|---|---|---|
| 27 | | 1.18 (2 min) | $[C_{22}H_{17}{}^{35}Cl_2NO_4$ $M + H]^+$ 430 | Allowed to cool to room temperature overnight. Product precipitated on cooling, collected by filtration and dried under vacuum |
| 28 | | 3.19 (5 min) | $[C_{22}H_{16}{}^{35}Cl_3NO_4$ $M + H]^+$ 464 | Allowed to cool to room temperature overnight. Product precipitated on cooling, collected by filtration and dried under vacuum |
| 29 | | 1.28 (2 min) | $[C_{22}H_{16}{}^{35}Cl_3NO_4$ $M + H]^+$ 464 | Allowed to cool to room temperature overnight. Product precipitated on cooling, collected by filtration and dried under vacuum, further purified by MDAP. |
| 40 | | 1.21 (2 min) | $[C_{23}H_{18}{}^{35}ClF_2NO_4$ $M + H]^+$ 446 | Allowed to cool to room temperature overnight. Product precipitated on addition of water, collected by filtration and dried under vacuum |

The following examples 19, 20, 30-39 and 41 to 45 were prepared in a similar manner to (4-{[(6-Chloro-3-{[(3-chlorophenyl)methyl]oxy}-2-fluorophenyl)carbonyl]amino}phenyl)acetic acid (example 15) from the appropriate starting materials with any differences from the described procedure noted in the following table:

| Ex. No. | Compound | LC (method) | MS | Synthetic route/comments |
|---|---|---|---|---|
| 19 | | 1.17 (2 min) | $[C_{22}H_{16}{}^{35}Cl_2FNO_4$ $M + H]^+$ 447 | same as example 15 |

-continued

| Ex. No. | Compound | LC (method) | MS | Synthetic route/comments |
|---|---|---|---|---|
| 20 | (structure) | 1.22 (2 min) | [C$_{22}$H$_{15}$$^{35}$Cl$_3$FNO$_4$ M + H]$^+$ 481 | same as example 15 |
| 30 | (structure) | 1.21 (2 min) | [C$_{22}$H$_{16}$$^{35}$Cl$_2$FNO$_4$ M + H]$^+$ 447 | same as example 15 |
| 31 | (structure) | 1.27 (2 min) | [C$_{23}$H$_{19}$$^{35}$Cl$_2$NO$_4$ M + H]$^+$ 443 | same as example 15 |
| 32 | (structure) | 1.16 (2 min) | [C$_{23}$H$_{19}$F$_2$NO$_4$ M + H]$^+$ 412 | same as example 15 no MDAP |
| 33 | (structure) | 1.14 (2 min) | [C$_{24}$H$_{22}$FNO$_4$ M + H]$^+$ 408 | same as example 15 but longer reaction time (extra 6 hours), no MDAP |
| 34 | (structure) | 1.21 (2 min) | [C$_{24}$H$_{22}$FNO$_4$ M + H]$^+$ 408 | Heated to 65° C. for 2 hours. No MDAP |

| Ex. No. | Compound | LC (method) | MS | Synthetic route/comments |
|---|---|---|---|---|
| 35 | 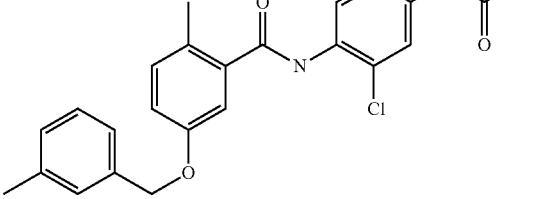 | 1.26 (2 min) | [C$_{24}$H$_{22}$$^{35}$ClNO$_4$ M + H]$^+$ 424 | Heated to 65° C. for 2 hours. No MDAP |
| 36 | 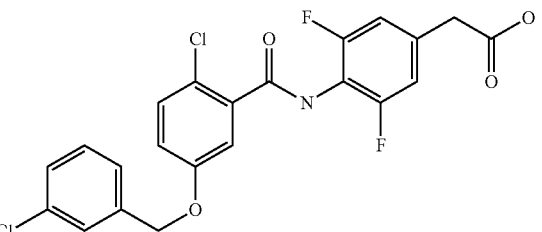 | 1.20 (2 min) | [C$_{22}$H$_{15}$$^{35}$Cl$_2$F$_2$NO$_4$ M + H]$^+$ 466 | same as example 15 but heated at 65° C. for 2 hours, no MDAP |
| 37 | 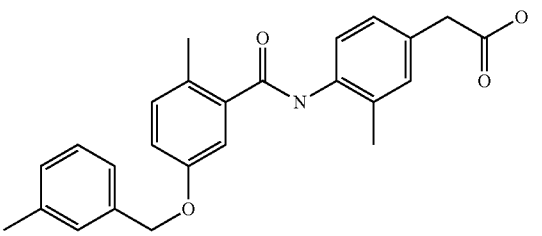 | 1.19 (2 min) | [C$_{25}$H$_{25}$NO$_4$ M + H]$^+$ 404 | Heated to 65° C. for 2 hours. No MDAP |
| 38 | 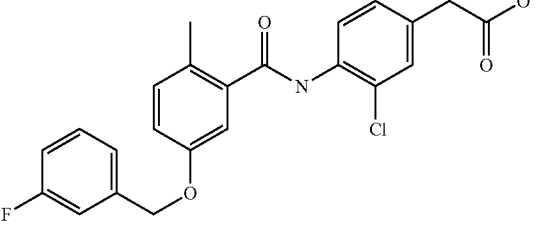 | 1.21 (2 min) | [C$_{23}$H$_{19}$$^{35}$ClFNO$_4$ M + H]$^+$ 428 | Heated to 65° C. for 2 hours. No MDAP |
| 39 | 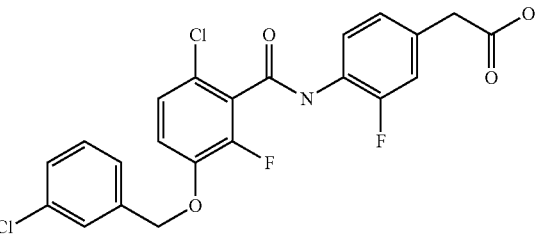 | 1.18 (2 min) | [C$_{22}$H$_{15}$$^{35}$Cl$_2$F$_2$NO$_4$ M + H]$^+$ 466 | same as example 15, no MDAP |
| 41 | 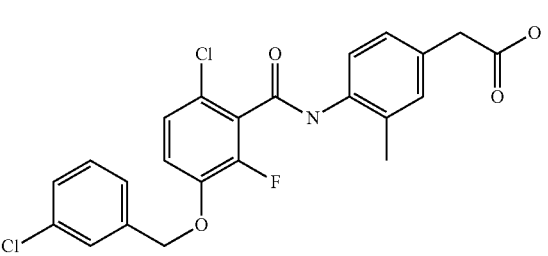 | 1.18 (2 min) | [C$_{23}$H$_{18}$$^{35}$Cl$_2$FNO$_4$ M + H]$^+$ 462 | same as example 15 |

-continued

| Ex. No. | Compound | LC (method) | MS | Synthetic route/comments |
|---|---|---|---|---|
| 42 | | 2.99 (5 min) | $[C_{22}H_{15}{}^{35}Cl_2F_2NO_4]$ $M+H]^+$ 466 | same as example 15 but stirred at RT only for 2 hours, not acidified, directly purified by MDAP after evaporation of solvent |
| 43 | | 2.92 (5 min) | $[C_{22}H_{15}{}^{35}ClF_3NO_4]$ $M+H]^+$ 450 | same as example 15 but stirred at RT only for 2 hours, not acidified, directly purified by MDAP after evaporation of solvent |
| 44 | | 2.89 (5 min) | $[C_{23}H_{18}{}^{35}ClF_2NO_4]$ $M+H]^+$ 446 | same as example 15 but stirred at RT only for 2 hours, not acidified, directly purified by MDAP after evaporation of solvent |
| 45 | | 1.18 (2 min) | $[C_{23}H_{18}{}^{35}ClF_2NO_4]$ $M+H]^+$ 446 | Heated to 65° C. for 2 hours. Acidified rection mixture extracted with EtOAc, organic phase dried and evaporated. |

The detailed experimental for the preparation of the compound of example 24 from the table hereinabove is as follows:

Intermediate 84 (3-chlorophenyl)methyl 5-{[(3-chlorophenyl)methyl]oxy}-2-methylbenzoate (Intermediate 43, Alkylation Step)

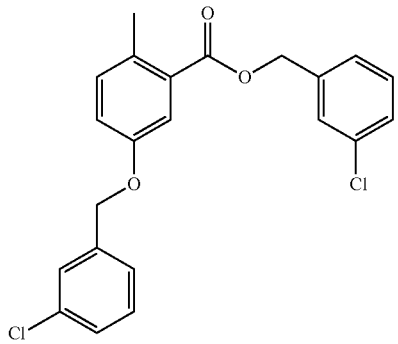

To a solution of 5-hydroxy-2-methylbenzoic acid (1.0 g, 6.6 mmol) in DMF (50 ml) were added potassium carbonate (1.82 g, 13.14 mmol, 2.0 eq) and 3-chlorobenzyl bromide (1.72 g, 13.14 mmol, 2.0 eq). The mixture was stirred at 70° C. for 2 hours and then left stirring at room temperature overnight. The temperature was increased to 80° C. and heating continued for a further 6 hours. After cooling the mixture was diluted with ethyl acetate (200 ml) and washed with water (2×200 ml). Organic layer was separated, dried over MgSO$_4$, filtered and evaporated to dryness to afford the title compound as a yellow oil, 2.67 g (contains 24% of monoalkylated phenol impurity). No further purification carried out. MS (ES−) m/z 399 [M−H]$^-$ (C$_{22}$H$_{18}$$^{35}$Cl$_2$O$_3$). $^1$H-NMR (400 MHz, CDCl3) δ 2.52 (3H, s), 5.04 (2H, s), 5.29 (2H, s), 7.02 (1H, dd, J 8.4, J 2.8), 7.16 (1H, d, J 8.4), 7.29-7.34 (6H, m), 7.43 (2H, d, J 1.2), 7.54 (1H, d, J 2.8).

Intermediate 85 5-{[(3-chlorophenyl)methyl]oxy}-2-methylbenzoic Acid (Intermediate 43, Hydrolysis Step)

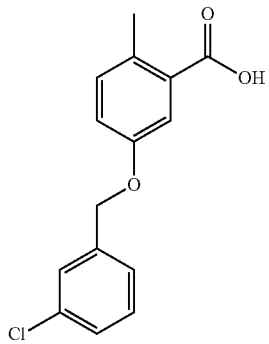

A solution of (3-chlorophenyl)methyl 5-{[(3-chlorophenyl)methyl]oxy}-2-methylbenzoate from the preparation of Intermediate 84 described above (2.67 g, 6.66 mmol) in 1,4-dioxane (20 ml) and water (10 ml) was treated with lithium hydroxide (419 mg, 9.99 mmol, 1.5 eq). The resulting mixture was stirred at room temperature under argon overnight. A further portion of lithium hydroxide (419 mg, 9.99 mmol, 1.5 eq) was added and stirring continued at room temperature for 2 hours. Stirring continued at room temperature overnight. The solvent was then evaporated to dryness and then partitioned between 2M HCl (100 ml) and diethylether (100 ml). The organic layer was separated and passed through a hydrophobic frit to remove any water and evaporated to dryness to afford the title compound as a white solid (1.98 g) (contains 12% impurity). No further purification carried out. MS (ES−) m/z 275 [M−H]$^-$ (C$_{15}$H$_{13}$$^{35}$ClO$_3$).

Intermediate 86 5-{[(3-chlorophenyl)methyl]oxy}-2-methylbenzoylchloride (Intermediate 62 Acid Chloride Formation)

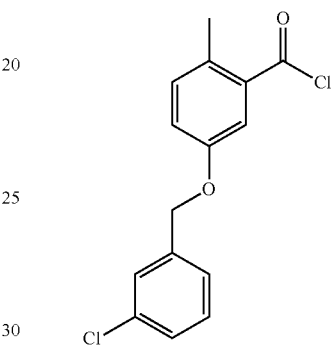

DMF (1 drop) was added to a suspension of 5-{[(3-chlorophenyl)methyl]oxy}-2-methylbenzoic acid from the preparation of Intermediate 85 as described above (200 mg, 0.72 mmol) and oxalyl chloride (95 ul, 1.08 mmol, 1.5 eq) in DCM (5 ml). The resulting mixture was stirred at room temperature for 1 hour. The reaction mixture was then evaporated to dryness and azeotroped with toluene (2×50 ml). The organic layer was separated, dried and evaporated in vacuo to afford the title compound as a yellow solid, 213 mgs. No further purification carried out. LCMS sample dissolved in methanol, MS (ES+) m/z 291 [M+H]$^+$ (C$_{16}$H$_{15}$$^{35}$ClO$_3$), corresponding to methyl ester generated from acid chloride.

Intermediate 87 Ethyl (4-{[(5-{[(3-chlorophenyl)methyl]oxy}-2-methylphenyl)carbonyl]amino}-3-methylphenyl)acetate (Intermediate 62, Amide Coupling)

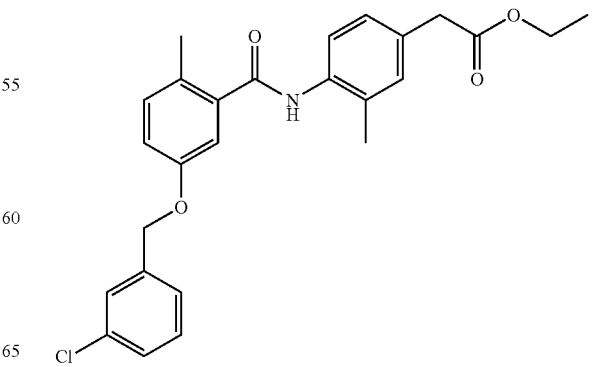

Triethylamine (74 ul, 0.53 mmol, 1.5 eq) was added to a suspension of 5-{[(3-chlorophenyl)methyl]oxy}-2-methylbenzoylchloride (105 mgs, 0.36 mmol) and ethyl (4-amino-3-methylphenyl)acetate (103 mg, 0.53 mmol, 1.5 eq) in dichloromethane (5 ml). The mixture was stirred at room temperature overnight. The mixture was then diluted with acetonitrile and purified by SCX cartridge (5 g) eluting with acetonitrile. Fractions containing product were combined and evaporated to give the title compound as a yellow gum, 174 mg. MS (ES+) m/z 452 [M+H]$^+$ (C$_{26}$H$_{26}$$^{35}$ClNO$_4$).

Example 46

(4-{[(5-{[(3-chlorophenyl)methyl]oxy}-2-methylphenyl)carbonyl]amino}-3-methylphenyl)acetic Acid (Example 24)

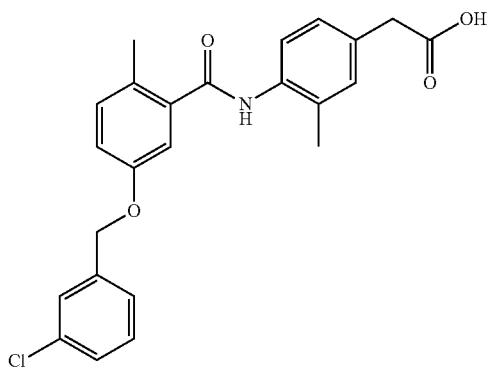

Ethyl (4-{[(5-{[(3-chlorophenyl)methyl]oxy}-2-methylphenyl)carbonyl]amino}-3-methylphenyl)acetate (174 mg, 0.39 mmol) was taken up in acetic acid (10 ml) and 2M HCl (10 ml) and heated at 90° C. for 2 hours. The reaction mixture was allowed to cool and stirring continued at room temperature overnight. The reaction mixture was extracted with ethyl acetate (50 mls), dried using a hydrophobic frit and then evaporated to dryness to give a yellow solid/gum, 155 mg. This was purified by MDAP to give the title compound as a white solid, 39 mg. MS (ES+) m/z 424 [M+H]$^+$ (C$_{24}$H$_{22}$$^{35}$ClNO$_4$). $^1$H-NMR (400 MHz, d$_6$-DMSO) δ 2.24 (3H, s), 2.34 (3H, s), 3.52 (2H, s), 5.17 (2H, s), 7.02-7.15 (4H, m), 7.22 (1H, d, J 8.4), 7.31 (1H, d, J 8.0), 7.39-7.44 (3H, m), 7.53 (1H, s), 9.71 (1H, s), 12.33 (1H, bs).

The compound of example 24 was also prepared at larger scale using the following method. Other compounds of the present invention may be made at larger scale using similar methods.

Intermediate 88: Ethyl 5-hydroxy-2-methylbenzoate

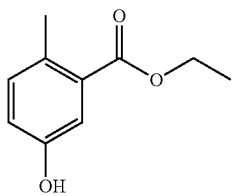

Aluminium chloride (97 g, 731 mmol) was added over 30 seconds to stirred DCM (3 L) under argon at 16° C. resulting in a temp rise to 20° C. When this had dissolved (approx 5 mins) and the temp had cooled to 18° C., ethyl-2-propynate (71.7 g, 731 mmol) was added. A solution of 2-methylfuran (60 g, 731 mmol) in DCM (600 ml) was added to the stirred solution over 35 minutes resulting in a measured exotherm 20.5° C. The exotherm was controlled by a Huber cooling unit and the observed temp range during the addition was 18° C.-20.5° C. After the addition was complete the brown reaction mixture was stirred at 20° C. After a total of 50 mins at 20° C., the reaction mixture was poured into water (3 L) and ice (1 Kg) with stirring to give a yellow mixture. This was transferred to a separating funnel and shaken vigorously. The layers were separated and the aqueous phase further extracted with DCM (1 L). The combined organic extracts were rewashed with water (1.5 L), dried (Na$_2$SO$_4$) and filtered through Kieselguhr. The filtrate was concentrated in vacuo to a brown/green oil. This was purified by silica gel flash chromatography on 2 Biotage 75 L columns in toluene (700 ml) and the solution split into 2 equal portions and each passed through a 75 L column, collecting 400 ml fractions and eluting with the following solvent eluant systems:

1st Column:

toluene (3 L)

acetone/toluene (3:97) (2.5 L)

acetone/toluene (6:94) (2.5 L)

acetone/toluene (9:91) (2.5 L)

A moderate separation was achieved. Fraction 14 was recycled into 2nd column separation Fractions 15-17 combined and contained product 2nd Column:

toluene (3 L)

acetone/toluene (1:99) (2.5 L)

acetone/toluene (3:97) (2.5 L)

acetone/toluene (4:96) (2.5 L)

acetone/toluene (5:95) (2.5 L)

Moderate separation achieved. Fraction 17 was mixture and recycled (17 g) into 3rd column separation.

Fraction 18-23 combined and contained product.

3rd Column:

The mixture was applied as a solution in toluene (50 ml) to a Biotage 75M column, eluting as follows and collecting 200 ml fractions.

ethyl acetate/iso-hexane (5:95) (1.5 L)

ethyl acetate/iso-hexane (1:9) (2.5 L)

ethyl acetate/iso-hexane (15:85) (0.2 L)

Reasonable separation achieved.

Fractions 19-28 combined and contained product.

Pooling of Product Fractions

F15-17 (C1)

F18-23 (C2)

F19-28 (C3)

combined and concentrated in vacuo to a yellow oil which solidified on drying at rt under vacuum for 4 h: Wt=41.7 g, (0.231 mol, 32%). MS (ES$^-$) [C$_{10}$H$_{12}$O$_3$—H]$^-$ 179. $^1$H-NMR (400 MHz) δ 1.38 (3H, t, J 7.2), 2.51 (3H, s), 4.35 (2H, q, J 7.2), 5.36 (1H, s), 6.91 (1H, dd, J 8.4, 2.8), 7.10 (1H, d, J 8.0), 7.43 (1H, d, J 2.8).

Intermediate 89: Ethyl 5-{[(3-chlorophenyl)methyl]oxy}-2-methylbenzoate

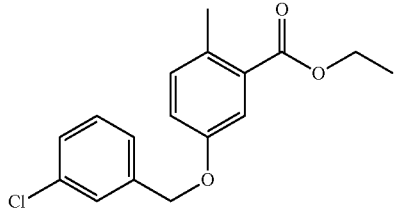

A suspension of ethyl 5-hydroxy-2-methylbenzoate (39.06 g, 217 mmol), 3-chlorobenzyl bromide (31.3 ml, 238 mmol) and potassium carbonate (44.9 g, 325 mmol) in N,N-dimethylformamide (1000 ml) was stirred at room temperature for 18 hours. The reaction was then filtered, diluted with ethyl acetate (2 L), washed with water (2 L then 3×1 L) and brine (1 L), filtered through a hydrophobic frit and concentrated to give the title compound as a dark yellow oil (68.61 g) which was used without further purification. MS (ES$^+$) [$C_{17}H_{17}{}^{35}ClO_3$+H]$^+$ 305. $^1$H-NMR (400 MHz, d$_6$-DMSO) δ 1.31 (3H, t, J 7.2), 2.42 (3H, s), 4.28 (2H, q, J 7.2), 5.14 (2H, 2), 7.13-7.16 (1H, m), 7.19-7.23 (1H, m), 7.33-7.45 (4H, m), 7.54-7.55 (1H, m).

Intermediate 90: 5-{[(3-chlorophenyl)methyl]oxy}-2-methylbenzoic Acid (Intermediate 43)

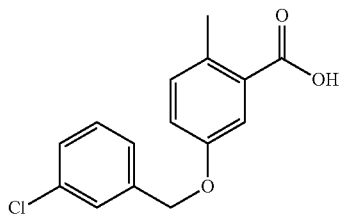

Lithium hydroxide (16.3 g, 389 mmol) was added to a solution of ethyl 5-{[(3-chlorophenyl)methyl]oxy}-2-methylbenzoate (79 g, 259 mmol) in 1,4-dioxane (1 L) and water (0.5 L). The reaction mixture was stirred at 65° C. for 5 hours, allowed to cool and stood at room temperature for 14 hours. The reaction was concentrated to remove the 1,4-dioxane, and the resulting brown aqueous solution was washed with diethyl ether (3×1 L). The aqueous layer was then acidified with 2N HCl (approximately 200 ml) and the resulting precipitate filtered and washed with water to give a yellow solid. This was dried overnight at 40° C. in a vacuum oven to give the title compound as a yellow solid (66.38 g). MS (ES$^-$) [$C_{15}H_{13}{}^{35}ClO_3$—H]$^-$ 275. $^1$H-NMR (400 MHz, d$_6$-DMSO) δ 2.43 (3H, s), 5.14 (2H, s), 7.10-7.13 (1H, m), 7.21-7.23 (1H, m), 7.38-7.47 (4H, m), 7.52 (1H, s).

Intermediate 91 Ethyl phenylmethyl (3-methyl-4-nitrophenyl)propanedioate

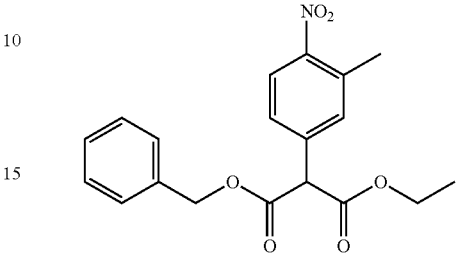

Sodium Hydride (19.09 g, 477 mmol) was added portionwise over 30 minutes to an ice cooled solution of ethyl phenylmethyl propanedioate (115 ml, 477 mmol) in DMF (500 ml). Upon complete addition, the reaction was allowed to warm to room temperature. After stirring for 30 minutes, a solution of 4-fluoro-2-methyl-1-nitrobenzene (30 ml, 239 mmol) in DMF (250 ml) was added, the reaction heated to 100° C. and stirred at this temperature for 16 hours under an atmosphere of argon. The reaction was then left to stand at room temperature for 72 hours. The reaction was quenched with concentrated HCl (~100 ml) with stirring and cooling (ice bath), diluted with ethyl acetate (2 L), washed with water (3×2 L), brine (1 L), dried over sodium sulfate, filtered and concentrated to give a dark yellow oil (~150 g). Purification was by silica chromatography, 1500 g cartridge, sample loaded as a toluene solution to the pre-conditioned column). A gradient of 0 to 5% acetone in pentane eluted the higher running component, this was followed by a gradient of 5 to 15% acetone in isohexane to elute the excess benzyl ethyl malonate and required product. Product-containing fractions were concentrated to give the title compound as a pale yellow oil (71.21 g). MS (ES–) [$C_{19}H_{19}NO_6$—H]$^-$ 356. $^1$H-NMR (400 MHz, d$_6$-DMSO) δ 1.14 (3H, t, J 7), 2.50 (3H, s), 4.01-4.21 (2H, m), 5.14-5.25 (2H, m), 5.27 (1H, s), 7.28-7.49 (7H, m), 8.00 (1H, d, J 8)

Intermediate 92 Ethyl (4-amino-3-methylphenyl)acetate (Intermediate 10)

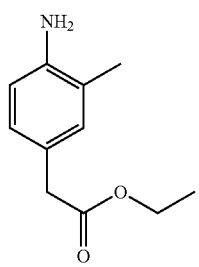

Batch 1: Ethyl phenylmethyl (3-methyl-4-nitrophenyl)propanedioate (35 g, 98 mmol) was taken up in Ethanol (500 ml) and subjected to a hydrogenation at atmospheric pressure using 10% palladium on carbon (3.13 g, 2.94 mmol). After 18 hours a small sample was removed for analysis. The catalyst was removed by filtration through celite and fresh catalyst palladium on carbon (3.13 g, 2.94 mmol) was added to the reaction mixture. The reaction was put on again for 3 hours. The hydrogenation continued for a further 3 hours. The hydrogenation reservoir was refilled and the reaction continued overnight. The catalyst was removed by filtration through celite and fresh catalyst palladium on carbon (3.13 g, 2.94 mmol) was added to the reaction mixture. The reaction was put on again for 3 hours. After the weekend stirring under these conditions, the reaction mixture added to the equivalent reaction mixture from Batch 2.

Batch 2: ethyl phenylmethyl (3-methyl-4-nitrophenyl)propanedioate (35 g, 98 mmol) was taken up in Ethanol (500 ml) and subjected to a hydrogenation at atmospheric pressure using 10% palladium on carbon (3.13 g, 2.94 mmol). After 2 hours a sample was taken for analysis. The reservoir was refilled with hydrogen and the reaction continued overnight. The catalyst was removed by filtration through celite and fresh catalyst palladium on carbon (3.13 g, 2.94 mmol) was added to the reaction mixture. The reaction was put on again for 3 hours. After leaving the reaction mixture under these conditions for the weekend, it was combined with BATCH 1 reaction mixture (equivalent reaction mixture) and filtered through celite to give a colourless filtrate. This solution was concentrated to an oily solid (wt=31.9 g). To this mixture was added toluene (200 ml) and the mixture was filtered from an insoluble white gum (wt=0.65 g). The filtrate was passed down a silica gel Biotage 75 L chromatography column eluting with the following ethyl acetate/iso-hexane gradient mixture and collecting 400 ml fractions:
ethyl acetate/iso-hexane
440 ml:2500 ml (15%)
833:2500 ml (25%)
1000:1900 ml (35%)
800:1250 ml (40%)

Fractions 13-19 were combined and concentrated to give the title compound as an oil which solidified on drying for 2 hours at room temperature under vacuum (wt=24.5 g). MS (ES$^+$) [C$_{11}$H$_{15}$NO$_2$+H]$^+$ 194. $^1$H-NMR (400 MHz, d$_6$-CDCl$_3$) δ 1.25 (3H, t, J 7), 2.15 (3H, s), 3.48 (s, 2H), 3.56 (2H, br. s), 4.13 (2H, q, J 7), 6.63 (1H, d, J 8), 6.93-6.97 (2H, m).

Intermediate 93: ethyl (4-{[(5-{[(3-chlorophenyl)methyl]oxy}-2-methylphenyl)carbonyl]amino}-3-methylphenyl)acetate (Intermediate 62)

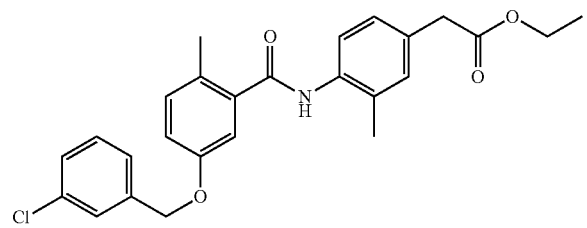

Oxalyl chloride (15.1 ml, 173 mmol) was added over approx 1 minute to a stirred suspension of 5-{[(3-chlorophenyl)methyl]oxy}-2-methylbenzoic acid (31.8 g, 115 mmol) in dichloromethane (1.14 L) at 20° C. under argon. This was followed by the addition of N,N dimethylformamide (2 ml, 25.8 mmol) over 3 minutes with accompanying gas evolution but no noticeable temperature rise. Within approx 15 minutes the suspension dissolved and turned a darker brown. The mixture was stirred under argon at 20° C. for a total of 75 minutes. After 75 minutes the reaction mixture was evaporated in vacuo to a cream solid which was dried under vacuum at room temperature for 1 h. The solid was then redissolved in dichloromethane (900 ml) and to the stirred solution at 20° C. under argon was simultaneously added a solution of ethyl (4-amino-3-methylphenyl)acetate (24.4 g, 126 mmol) in dichloromethane (240 ml) and triethylamine (24 ml) over 10-15 minutes. The temperature rise in the reaction was from 20° C. to 30° C. over this time and thereafter slowly cooled to ambient. The brown solution was stirred under argon at room temperature for 14 h. After 14 h stirring the brown solution was washed with water (2×1 L). The combined aqueous washes were re-extracted with dichloromethane (500 ml) and all the organic extracts were combined, dried (MgSO$_4$) and evaporated in vacuo to a brown oily solid which was dried at room temperature, under vacuum for 0.5 hours (wt=51.7 g). This material was dissolved in dichloromethane (200 ml) and the solution column chromatographed on Biotage 75 L system eluting with an ethyl acetate/iso-hexane gradient mixture and collecting 400 ml fractions as follows:
ethyl acetate/iso-hexane 440 ml/2500 ml (15%)
833 ml/2500 ml (25%)
2016 ml/3750 ml (35%)

Fractions 15-20 were combined and concentrated to a pink solid, dried at room temperature under vacuum for 2 hours (Wt=43.2 g). The solid was stirred with diethyl ether (100 ml) for 1 h at room temperature to remove most of the colour in the supernatant. The off-white solid was filtered and dried at 40° C. under vacuum for 4 hours. Wt=40.8 g. MS (ES$^+$) [C$_{26}$H$_{26}$$^{35}$ClNO$_4$$^+$H]$^+$ 452. $^1$H-NMR (400 MHz) δ 1.26 (3H, t, J 7.2), 2.26 (3H, s), 2.45 (3H, s), 3.57 (2H, s), 4.15 (2H, q, J 7.2), 5.06 (2H, s), 6.95-7.33 (10H, m), 7.94 (1H, d, J 8)

Example 47

(4-{[(5-{[(3-chlorophenyl)methyl]oxy}-2-methylphenyl)carbonyl]amino}-3-methylphenyl)acetic Acid (the Compound of Example 24)

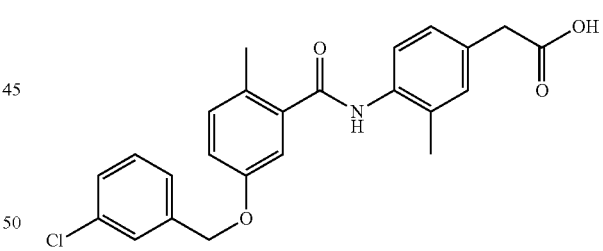

Method

To a stirred solution of ethyl (4-{[(5-{[(3-chlorophenyl)methyl]oxy}-2-methylphenyl)carbonyl]amino}-3-methylphenyl)acetate (39.8 g, 88 mmol) in 1,4-dioxane (700 ml) at ambient temp. under argon was added a solution of lithium hydroxide monohydrate (5.5 g, 131 mmol) in water (400 ml) and the stirred pink solution was then heated to a block temperature of 65° C. The following internal temps were noted during the course of the reaction:
t=0 mins 20° C.
t=40 mins 47° C.
t=60 mins 50° C.
t=75 mins 50° C.

After 75 mins the reaction mixture was cooled to 40° C. and concentrated in vacuo (bath temp 40° C.) to remove 650 ml of solvent, at which time crystallisation began to occur in the reaction mixture. At this point 2M hydrochloric acid (150 ml) was added to the mixture causing further crystallisation and turning the colour from pink to yellow. The supernatant was measured as pH1 and the mixture was further concentrated to remove another 80 ml of solvent. The stirred mixture was then cooled to 5° C. in an ice bath and after 0.5 h it was filtered off and washed with water (3×150 ml), sucked dry then further dried at 40° C., under vacuum, for 20 hours (wt=37.4 g). MS (ES+) $[C_{24}H_{22}{}^{35}ClNO_4{}^+H]^+$ 424. $^1$H-NMR (400 MHz, $d_6$-DMSO) δ 2.24 (3H, s), 2.35 (3H, s), 3.53 (2H, s), 5.17 (2H, s), 7.02-7.53 (10H, m), 9.72 (1H, s), 12.35 (1H, br. s).

Biological Data

Studies were performed using HEK-293(T) cells expressing the recombinant human prostanoid $EP_4$ receptor (HEK-$EP_4$ cells). Cells were grown as a monolayer culture in DMEM-F12/F12 containing glutamax II™ (a source of L-Glutamine) (Gibco) and supplemented with 10% foetal bovine serum (Gibco) and 0.4 mg·ml-1 G418. HEK-$EP_4$ cells were pre-treated 24 hr and 30 mins prior to the experiment with 10 μM indomethacin and harvested using Versene™ (EDTA) containing 10 μM indomethacin. The cells were resuspended in assay buffer (DMEM:F12, 10M indomethacin and 200 μM IBMX) at $1\times10^6$ cells per ml and incubated for 20 min at 37° C. Thereafter, 50 μl of cells were added to 50 μl test compound (compound of Formula (I)) and incubated at 37° C. for 4 minutes before stopping reactions with 100 μl of 1% Triton® X-100 (non-ionic surfactant). cAMP levels in the cell lysates were determined using a competition binding assay. In this assay the ability of cell lysates to inhibit 3H-cAMP (Amersham) binding to the binding subunit of protein kinase A was measured and cAMP levels were calculated from a standard curve. The data for each compound were expressed as a % of the response to a 10 nM maximal concentration of the standard agonist $PGE_2$. For each compound the maximal response and concentration of compound causing 50% of its maximal response were calculated ($pEC_{50}$). Intrinsic activity is expressed relative to the maximal response to $PGE_2$ [(maximum response to test compound)*100/(maximum response to $PGE_2$)]. Unless stated, reagents were purchased commercially from Sigma.

The Examples of the present invention were tested in the above-mentioned assay and exhibited average $pEC_{50}$ values of 6.0 or higher, and average intrinsic activities of 20% or higher.

The invention claimed is:

1. A compound having the structure:

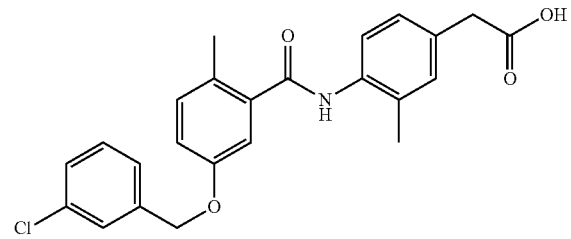

or a pharmaceutically acceptable salt thereof.

2. A pharmaceutical composition comprising the compound of claim 1 and a pharmaceutically acceptable carrier or diluent thereof.

* * * * *